US009821016B2

(12) United States Patent
Lauer et al.

(10) Patent No.: US 9,821,016 B2
(45) Date of Patent: Nov. 21, 2017

(54) GENETICALLY MODIFIED PARAMYXOVIRUS FOR TREATMENT OF TUMOR DISEASES

(71) Applicant: Eberhard-Karls-Universitaet Tuebingen Universitaetsklinikum, Tuebingen (DE)

(72) Inventors: Ulrich Manfred Lauer, Tuebingen (DE); Michael Bitzer, Rottenburg (DE); Martina Zimmermann, Tuebingen (DE); Sorin Armeanu-Ebinger, Tuebingen (DE); Sascha Bossow, Heidelberg (DE); Wolfgang Neubert, Greifenberg (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 0 days.

(21) Appl. No.: 13/656,913

(22) Filed: Oct. 22, 2012

(65) Prior Publication Data

US 2013/0078219 A1 Mar. 28, 2013

Related U.S. Application Data

(63) Continuation of application No. PCT/EP2011/056290, filed on Apr. 20, 2011.

(30) Foreign Application Priority Data

Apr. 23, 2010 (DE) ........................ 10 2010 018 961

(51) Int. Cl.

| | |
|---|---|
| ***A61K 48/00*** | (2006.01) |
| ***C07H 21/04*** | (2006.01) |
| ***A61K 35/76*** | (2015.01) |
| ***C07K 14/005*** | (2006.01) |
| ***A61K 35/768*** | (2015.01) |
| *A01K 67/00* | (2006.01) |
| *A61K 39/00* | (2006.01) |

(52) U.S. Cl.

CPC ............ *A61K 35/76* (2013.01); *A61K 35/768* (2013.01); *C07K 14/005* (2013.01); *A61K 2039/5256* (2013.01); *C12N 2760/18822* (2013.01); *C12N 2760/18832* (2013.01)

(58) Field of Classification Search

CPC ............ A61K 35/76; A61K 2039/5256; A61K 35/768; C12N 2760/18822; C12N 2760/18832; C07K 14/005

See application file for complete search history.

(56) References Cited

U.S. PATENT DOCUMENTS

| | | | | |
|---|---|---|---|---|
| 2004/0204581 | A1* | 10/2004 | Skiadopoulos et al. | 536/23.72 |
| 2009/0175826 | A1 | 7/2009 | Subbiah et al. | 424/93.2 |
| 2010/0196993 | A1 | 8/2010 | Nishimura et al. | 435/236 |

FOREIGN PATENT DOCUMENTS

EP 1 067 179 A1 * 10/2001

OTHER PUBLICATIONS

Panda et al. 2004. Role of fusion protein cleavage site in the virulence of Newcastle disease virus. Microbial Pathogenesis 36:1-10, 2004.*

Kinoh, H., et al. (2004) "Generation of a recombinant sendai virus that is selectively activated and lyses human tumor cells expressing matrix metalloproteinases" Gene Therapy, 11:1137-1145.

Kinoh, H., et al. (2009) "Generation of optimized and urokinase-targeted oncolytic sendai virus vectors applicable for various human malignancies" Gene Therapy, 16:392-403.

Oldoni, I., et al. (2005) "The use of in situ hybridization and immunohistochemistry to study the pathogenesis of various newcastle disease virus strains and recombinants in embryonated chicken eggs" Microbial Pathogenesis, 39:69-75.

Vähä-Koskela, M., et al. (2007) "Oncolytic viruses in cancer therapy" Cancer Letters, 254:178-216.

Kato, A., et al. (1997), "The paramyxovirus, Sendai virus, V protein encodes a luxury function required for viral pathogenesis", *The EMBO Journal*, 16(3): 578-587.

* cited by examiner

*Primary Examiner* — Quang Nguyen

(74) *Attorney, Agent, or Firm* — Harness, Dickey and Pierce, P.L.C.

(57) ABSTRACT

The present invention relates to a genetically modified Paramyxovirus, a pharmaceutical composition comprising this paramyxovirus, the use of a genetically modified Paramyxovirus for the therapeutic and/or prophylactic treatment of a tumor disease, and a method for the production of a pharmaceutical composition for the therapeutic or prophylactic treatment of a tumor disease.

15 Claims, 8 Drawing Sheets

5´
3´
SphI
1470bp
3065bp
EcoRI
3728bp
5323bp
2258 bp
2000f
2000bp
3595bp
2502 rev
2502bp
2654f
2654bp
4249bp
3326f
3326bp
4921bp
Eco P rev
3772bp
3758rev
2163bp
3758bp
3157rev
3157bp
608bp
654bp
672bp
402bp
~140bp
78bp
~100bp
~80bp
~250bp
ES
Y1, Y2
C
P
C´

A
Vero
Hep3B
HuH7
PLC/PRF/5
B
Vero
Hep3B
HuH7
PLC/PRF/5
TCID50
Zeit (h)
Fmut
FmutdV
Fmut dC
Fmut dCdY
Fmut dCdV
Fmut dCdYdV

SEQUENCE LISTING

```
<160> NUMBER OF SEQ ID NOS: 39

<210> SEQ ID NO 1
<211> LENGTH: 1698
<212> TYPE: DNA
<213> ORGANISM: Sendai virus
<220> FEATURE:
<223> OTHER INFORMATION: This is a combined DNA/RNA sequence.

<400> SEQUENCE: 1

atggcgactt atatccagag ggtacagtgc atatctgcat tattgtcagt tgtgctcaca     60

acactggtct cgtgtcaaat tcctagagat aggctctcta atataggggt catagtcgac    120

gaagggaaat cactgaagat tgccgggtcc cacgaatcta ggtacatcgt attaagtctg    180

gtcccaggga tagacctcga aaatgggtgc ggaacagctc aggttatcca gtataagagc    240

ctactgaacc ggttgttaat cccattgaga gatgccttag atcttcagga ggctctgata    300

actgtcacta atgacacgat gaccggtgct gatgtcccac agtcaagatt cttcggcgcc    360

gtgattggga ccatagcact tggagtggca acatcagcac agataaccgc agggatcgcg    420

ctagctgagg cgagggaggc caagagagac atagcactca taaaagaatc aatgacaaag    480

acacacaaat ctatagaact gctgcaaaac gctgtggggg aacaaattct tgctctaaag    540
```

```
acgctccagg atttcgtgaa tgatgagatc aaacccgcga taagcgaatt gggttgtgag    600

actgccgctt taagactggg gataaaactg acacaacatt actccgagct gctgactgca    660

tttggatcta actttggaac catcggagag aagagcctca cactgcaggc actgtcttca    720

ctctactctg ctaacatcac tgagattatg accacgatca ggacagggca gtccaacatc    780

tatgacgtca tttatacgga gcagatcaag ggaactgtga ttgatgtaga tctagagaga    840

tacatggtta ccctgtctgt aaaaatcccc attctttctg aagtcccagg tgtgcttata    900

cacaaagcat cgtctatttc ttacaatata gacggggagg agtggtatgt gactgtcccc    960

agtcacatac tcagtcgtgc ctccttcctg gggggtgcaa acatagctga ttgtgtagag   1020

tccagattga cctacatatg ccctagggat cctgcacaat tgatacctga cagccagcaa   1080

aaatgtatct tgggggacac aacaaggtgt cctgtcacaa aggttgtgga taacatcatc   1140

cccaaatttg cctttgtaaa tggaggtgtc gttgcgaact gcatagcatc cacatgtacc   1200

tgtgggacag gccgaaggcc aatcagtcag gatcgctcta aaggtgtagt attcttaact   1260

catgataact gtggactcat aggagtcaat gggatagaat tgtatgctaa taggaaaggg   1320

catgatgcca cttgggggt ccagaatttg acagtcggtc ctgcaatcgc tatcagaccc    1380

gtggacattt ctctcaacct tgccgctgct actgacttcc tgcaagactc tagagctgaa   1440

cttgagaagg cacgaaaaat cctctctgaa gtaggtagat ggtacaattc aggggcgact   1500

ttgattacga tcatagtagt catgattgta gtattggtgg tcattatagt gattgtcatt   1560

gtgctctaca gactcaggag atcaatgcta atgagtaatc cagccggtcg gatatcaaga   1620

gacacatata cattagagcc gaagataagg catatgtata ctaacggtgg gttcgatgct   1680

atgactgaga aaagatag                                                 1698
```

```
<210> SEQ ID NO 2
<211> LENGTH: 565
<212> TYPE: PRT
<213> ORGANISM: Sendai virus

<400> SEQUENCE: 2

Met Ala Thr Tyr Ile Gln Arg Val Gln Cys Ile Ser Ala Leu Leu Ser
1               5                   10                  15

Val Val Leu Thr Thr Leu Val Ser Cys Gln Ile Pro Arg Asp Arg Leu
            20                  25                  30

Ser Asn Ile Gly Val Ile Val Asp Glu Gly Lys Ser Leu Lys Ile Ala
        35                  40                  45

Gly Ser His Glu Ser Arg Tyr Ile Val Leu Ser Leu Val Pro Gly Ile
    50                  55                  60

Asp Leu Glu Asn Gly Cys Gly Thr Ala Gln Val Ile Gln Tyr Lys Ser
65                  70                  75                  80

Leu Leu Asn Arg Leu Leu Ile Pro Leu Arg Asp Ala Leu Asp Leu Gln
                85                  90                  95

Glu Ala Leu Ile Thr Val Thr Asn Asp Thr Met Thr Gly Ala Asp Val
            100                 105                 110

Pro Gln Ser Arg Phe Phe Gly Ala Val Ile Gly Thr Ile Ala Leu Gly
        115                 120                 125

Val Ala Thr Ser Ala Gln Ile Thr Ala Gly Ile Ala Leu Ala Glu Ala
    130                 135                 140

Arg Glu Ala Lys Arg Asp Ile Ala Leu Ile Lys Glu Ser Met Thr Lys
145                 150                 155                 160
```

```
Thr His Lys Ser Ile Glu Leu Leu Gln Asn Ala Val Gly Glu Gln Ile
                165                 170                 175

Leu Ala Leu Lys Thr Leu Gln Asp Phe Val Asn Asp Glu Ile Lys Pro
            180                 185                 190

Ala Ile Ser Glu Leu Gly Cys Glu Thr Ala Ala Leu Arg Leu Gly Ile
        195                 200                 205

Lys Leu Thr Gln His Tyr Ser Glu Leu Leu Thr Ala Phe Gly Ser Asn
    210                 215                 220

Phe Gly Thr Ile Gly Glu Lys Ser Leu Thr Leu Gln Ala Leu Ser Ser
225                 230                 235                 240

Leu Tyr Ser Ala Asn Ile Thr Glu Ile Met Thr Thr Ile Arg Thr Gly
                245                 250                 255

Gln Ser Asn Ile Tyr Asp Val Ile Tyr Thr Glu Gln Ile Lys Gly Thr
            260                 265                 270

Val Ile Asp Val Asp Leu Glu Arg Tyr Met Val Thr Leu Ser Val Lys
        275                 280                 285

Ile Pro Ile Leu Ser Glu Val Pro Gly Val Leu Ile His Lys Ala Ser
    290                 295                 300

Ser Ile Ser Tyr Asn Ile Asp Gly Glu Glu Trp Tyr Val Thr Val Pro
305                 310                 315                 320

Ser His Ile Leu Ser Arg Ala Ser Phe Leu Gly Gly Ala Asn Ile Ala
                325                 330                 335

Asp Cys Val Glu Ser Arg Leu Thr Tyr Ile Cys Pro Arg Asp Pro Ala
            340                 345                 350

Gln Leu Ile Pro Asp Ser Gln Gln Lys Cys Ile Leu Gly Asp Thr Thr
        355                 360                 365

Arg Cys Pro Val Thr Lys Val Val Asp Asn Ile Ile Pro Lys Phe Ala
    370                 375                 380

Phe Val Asn Gly Gly Val Val Ala Asn Cys Ile Ala Ser Thr Cys Thr
385                 390                 395                 400

Cys Gly Thr Gly Arg Arg Pro Ile Ser Gln Asp Arg Ser Lys Gly Val
                405                 410                 415

Val Phe Leu Thr His Asp Asn Cys Gly Leu Ile Gly Val Asn Gly Ile
            420                 425                 430

Glu Leu Tyr Ala Asn Arg Lys Gly His Asp Ala Thr Trp Gly Val Gln
        435                 440                 445

Asn Leu Thr Val Gly Pro Ala Ile Ala Ile Arg Pro Val Asp Ile Ser
    450                 455                 460

Leu Asn Leu Ala Ala Ala Thr Asp Phe Leu Gln Asp Ser Arg Ala Glu
465                 470                 475                 480

Leu Glu Lys Ala Arg Lys Ile Leu Ser Glu Val Gly Arg Trp Tyr Asn
                485                 490                 495

Ser Gly Ala Thr Leu Ile Thr Ile Ile Val Val Met Ile Val Val Leu
            500                 505                 510

Val Val Ile Ile Val Ile Val Ile Val Leu Tyr Arg Leu Arg Arg Ser
        515                 520                 525

Met Leu Met Ser Asn Pro Ala Gly Arg Ile Ser Arg Asp Thr Tyr Thr
    530                 535                 540

Leu Glu Pro Lys Ile Arg His Met Tyr Thr Asn Gly Gly Phe Asp Ala
545                 550                 555                 560

Met Thr Glu Lys Arg
                565
```

```
<210> SEQ ID NO 3
<211> LENGTH: 1707
<212> TYPE: DNA
<213> ORGANISM: Sendai virus
<220> FEATURE:
<223> OTHER INFORMATION: This is a combined DNA/RNA sequence.

<400> SEQUENCE: 3

atggatcaag atgccctcat ttctaaagaa gattctgaag ttgagaggga ggcgtcagga      60

ggacgagagt cgctctcgga tgttatcgga ttcctcgacg cagtcctatc aagtgaacca     120

actgacatcg gaggggacag aagctggctc cacaatacca tcaacaccct ccaaaggcca     180

ggctctaccc acagagtcaa aggtgagggc gagggagaag tctcgacatc gtcgacccaa     240

gataatcgat caggtgagga gagtagagtc tctgggggaa caagcgagcc agaggcagaa     300

gcacatgcta gaaacgttga taaacaaaat atacactggg ccactgggag aggagctagt     360

acagactctg tacctcagga tctgggcaat ggaagagact ccggaatcct tgaagatcct     420

ccaaatgagg gaggatatcc gagatcaggt gctgaagatg aaaaccgaga gatggctgcg     480

aaccctgata agaggggaga agaccaagct gaaggacttc cagaagagat acgaagaagt     540

gcacccctac ctgatgaaag agaaggtaga gcagataata atggaagagg cgtggagcct     600

ggcagcccac atagtgcaag agtgactgga gtcttggtga tccccagtcc tgagctcgaa     660

gaggccgtgc tacaaaggaa caagagacga cccgccaaca gcgggtccag atctctcacc     720

ccagtggtcg tgcctagcac tcggtctcca ccaccggacc atgacaatag tacaaggtca     780

ccaccaagga aacccccaac cacgcaggat gagcacacca accccaggaa cacccccgcc     840

gtcaggatca aggatcggag acccccaaca gggactcgct ccgccccaga ccgcccgacc     900

gacggctatc caacccaccc aagtccagag accgatgcaa caaaaaaggg catagaagag     960

aacacatcat ctatgaaaga gatggctaca ttgttaacga gtcttggtgt aatccagtct    1020

gctcaagaat tcgagtcgtc ccgagacgcg agttatgtgt ttgcaaagcg tgccctaaaa    1080

tctgcaaact atgcagagat ggcatttaat gtatgcggct tgatcctttc tgctgagaaa    1140

tctttcgcca atagagtaga cgagaataaa cagctgctta aacagatcca agaaagtgta    1200

gagtcatttc gggacatata caagagattc tctgagtatc agaaggaaca gaactcactg    1260

ctgatgtcta acctatctac ccttcatatt atcacagaca gaggtggcaa gactgacaat    1320

ccagattctc ccacaaggtc cccctctgtt tttgcaaaaa caaaagagaa caagaccaaa    1380

gcaactaggt ttgacccgtc tatggagacc atgggggata tgaggtataa accagaccta    1440

ctccgagagg atgaatttag agaagagatc cgcaacccgg tgtaccagga aagagatacc    1500

gaacccagag catccaatgc atcacgtctg cttccatcaa gagagaagcc tacaatacac    1560

tccctcaagc tcgtcataga gagcagtccc ctaagcagag ctgaaaaggc agcatatgtg    1620

aaatcattat ccaagtgcaa gacagaccaa gaagttaagg ccgtcatgga gcttgtagaa    1680

gaagacatag aatcactgac taattaa                                        1707


<210> SEQ ID NO 4
<211> LENGTH: 568
<212> TYPE: PRT
<213> ORGANISM: Sendai virus

<400> SEQUENCE: 4

Met Asp Gln Asp Ala Leu Ile Ser Lys Glu Asp Ser Glu Val Glu Arg
1               5                   10                  15

Glu Ala Ser Gly Gly Arg Glu Ser Leu Ser Asp Val Ile Gly Phe Leu
```

-continued

```
            20                  25                  30

Asp Ala Val Leu Ser Ser Glu Pro Thr Asp Ile Gly Gly Asp Arg Ser
        35                  40                  45

Trp Leu His Asn Thr Ile Asn Thr Leu Gln Arg Pro Gly Ser Thr His
    50                  55                  60

Arg Val Lys Gly Glu Gly Glu Gly Glu Val Ser Thr Ser Ser Thr Gln
65                  70                  75                  80

Asp Asn Arg Ser Gly Glu Glu Ser Arg Val Ser Gly Gly Thr Ser Glu
                85                  90                  95

Pro Glu Ala Glu Ala His Ala Arg Asn Val Asp Lys Gln Asn Ile His
            100                 105                 110

Trp Ala Thr Gly Arg Gly Ala Ser Thr Asp Ser Val Pro Gln Asp Leu
        115                 120                 125

Gly Asn Gly Arg Asp Ser Gly Ile Leu Glu Asp Pro Pro Asn Glu Gly
    130                 135                 140

Gly Tyr Pro Arg Ser Gly Ala Glu Asp Glu Asn Arg Glu Met Ala Ala
145                 150                 155                 160

Asn Pro Asp Lys Arg Gly Glu Asp Gln Ala Glu Gly Leu Pro Glu Glu
                165                 170                 175

Ile Arg Arg Ser Ala Pro Leu Pro Asp Glu Arg Glu Gly Arg Ala Asp
            180                 185                 190

Asn Asn Gly Arg Gly Val Glu Pro Gly Ser Pro His Ser Ala Arg Val
        195                 200                 205

Thr Gly Val Leu Val Ile Pro Ser Pro Glu Leu Glu Glu Ala Val Leu
    210                 215                 220

Gln Arg Asn Lys Arg Arg Pro Ala Asn Ser Gly Ser Arg Ser Leu Thr
225                 230                 235                 240

Pro Val Val Val Pro Ser Thr Arg Ser Pro Pro Pro Asp His Asp Asn
                245                 250                 255

Ser Thr Arg Ser Pro Pro Arg Lys Pro Pro Thr Thr Gln Asp Glu His
            260                 265                 270

Thr Asn Pro Arg Asn Thr Pro Ala Val Arg Ile Lys Asp Arg Arg Pro
        275                 280                 285

Pro Thr Gly Thr Arg Ser Ala Pro Asp Arg Pro Thr Asp Gly Tyr Pro
    290                 295                 300

Thr His Pro Ser Pro Glu Thr Asp Ala Thr Lys Lys Gly Ile Glu Glu
305                 310                 315                 320

Asn Thr Ser Ser Met Lys Glu Met Ala Thr Leu Leu Thr Ser Leu Gly
                325                 330                 335

Val Ile Gln Ser Ala Gln Glu Phe Glu Ser Ser Arg Asp Ala Ser Tyr
            340                 345                 350

Val Phe Ala Lys Arg Ala Leu Lys Ser Ala Asn Tyr Ala Glu Met Ala
        355                 360                 365

Phe Asn Val Cys Gly Leu Ile Leu Ser Ala Glu Lys Ser Phe Ala Asn
    370                 375                 380

Arg Val Asp Glu Asn Lys Gln Leu Leu Lys Gln Ile Gln Glu Ser Val
385                 390                 395                 400

Glu Ser Phe Arg Asp Ile Tyr Lys Arg Phe Ser Glu Tyr Gln Lys Glu
                405                 410                 415

Gln Asn Ser Leu Leu Met Ser Asn Leu Ser Thr Leu His Ile Ile Thr
            420                 425                 430

Asp Arg Gly Gly Lys Thr Asp Asn Pro Asp Ser Pro Thr Arg Ser Pro
        435                 440                 445
```

```
Ser Val Phe Ala Lys Thr Lys Glu Asn Lys Thr Lys Ala Thr Arg Phe
    450                 455                 460

Asp Pro Ser Met Glu Thr Met Gly Asp Met Arg Tyr Lys Pro Asp Leu
465                 470                 475                 480

Leu Arg Glu Asp Glu Phe Arg Glu Glu Ile Arg Asn Pro Val Tyr Gln
                485                 490                 495

Glu Arg Asp Thr Glu Pro Arg Ala Ser Asn Ala Ser Arg Leu Leu Pro
            500                 505                 510

Ser Arg Glu Lys Pro Thr Ile His Ser Leu Lys Leu Val Ile Glu Ser
        515                 520                 525

Ser Pro Leu Ser Arg Ala Glu Lys Ala Ala Tyr Val Lys Ser Leu Ser
    530                 535                 540

Lys Cys Lys Thr Asp Gln Glu Val Lys Ala Val Met Glu Leu Val Glu
545                 550                 555                 560

Glu Asp Ile Glu Ser Leu Thr Asn
                565


<210> SEQ ID NO 5
<211> LENGTH: 5
<212> TYPE: PRT
<213> ORGANISM: Sendai virus

<400> SEQUENCE: 5

Val Pro Gln Ser Arg
1               5


<210> SEQ ID NO 6
<211> LENGTH: 5
<212> TYPE: PRT
<213> ORGANISM: Newcastle disease virus

<400> SEQUENCE: 6

Arg Arg Gln Lys Arg
1               5


<210> SEQ ID NO 7
<211> LENGTH: 348
<212> TYPE: DNA
<213> ORGANISM: Sendai virus
<220> FEATURE:
<223> OTHER INFORMATION: This is a combined DNA/RNA sequence.

<400> SEQUENCE: 7

acggcttcgg ctacacttcc cgcatggatc aagatgccct catttctaaa gaagattctg      60

aagttgagag ggaggcgtca ggaggacgag agtcgctctc ggatgttatc ggattcctcg     120

acgcagtcct atcaagtgaa ccaactgaca tcggaggga cagaagctgg ctccacaata      180

ccatcaacac cctccaaagg ccaggctcta cccacagagt caaaggtgag ggcgagggag     240

aagtctcgac atcgtcgacc caagataatc gatcaggtga ggagagtaga gtctctgggg     300

gaacaagcga gccagaggca gaagcacatg ctagaaacgt tgataaac                  348


<210> SEQ ID NO 8
<211> LENGTH: 215
<212> TYPE: PRT
<213> ORGANISM: Sendai virus

<400> SEQUENCE: 8

Thr Ala Ser Ala Thr Leu Pro Ala Trp Ile Lys Met Pro Ser Phe Leu
1               5                   10                  15
```

```
Lys Lys Ile Leu Lys Leu Arg Gly Arg Arg Gln Glu Asp Glu Ser Arg
            20                  25                  30

Ser Arg Met Leu Ser Asp Ser Ser Thr Gln Ser Tyr Gln Val Asn Gln
        35                  40                  45

Leu Thr Ser Glu Gly Thr Glu Ala Gly Ser Thr Ile Pro Ser Thr Pro
    50                  55                  60

Ser Lys Gly Gln Ala Leu Pro Thr Glu Ser Lys Val Arg Ala Arg Glu
65                  70                  75                  80

Lys Ser Arg His Arg Arg Pro Lys Ile Ile Asp Gln Val Arg Arg Val
                85                  90                  95

Glu Ser Leu Gly Glu Gln Ala Ser Gln Arg Gln Lys His Met Leu Glu
            100                 105                 110

Thr Leu Ile Asn Lys Ile Tyr Thr Gly Pro Leu Gly Glu Glu Leu Val
        115                 120                 125

Gln Thr Leu Tyr Leu Arg Ile Trp Ala Met Glu Glu Thr Pro Glu Ser
    130                 135                 140

Leu Lys Ile Leu Gln Met Arg Glu Asp Ile Arg Asp Gln Val Leu Lys
145                 150                 155                 160

Met Lys Thr Glu Arg Trp Leu Arg Thr Leu Ile Arg Gly Glu Lys Thr
                165                 170                 175

Lys Leu Lys Asp Phe Gln Lys Arg Tyr Glu Glu Val His Pro Tyr Leu
            180                 185                 190

Met Lys Glu Lys Val Glu Gln Ile Ile Met Glu Glu Ala Trp Ser Leu
        195                 200                 205

Ala Ala His Ile Val Gln Glu
    210                 215
```

```
<210> SEQ ID NO 9
<211> LENGTH: 615
<212> TYPE: DNA
<213> ORGANISM: Sendai virus
<220> FEATURE:
<223> OTHER INFORMATION: This is a combined DNA/RNA sequence.

<400> SEQUENCE: 9

atgccctcat ttctaaagaa gattctgaag ttgagaggga ggcgtcagga ggacgagagt      60

cgctctcgga tgttatcgga ttcctcgacg cagtcctatc aagtgaacca actgacatcg     120

gaggggacag aagctggctc cacaatacca tcaacaccct ccaaaggcca ggctctaccc     180

acagagtcaa aggtgagggc gagggagaag tctcgacatc gtcgacccaa gataatcgat     240

caggtgagga gagtagagtc tctgggggaa caagcgagcc agaggcagaa gcacatgcta     300

gaaacgttga taaacaaaat atacactggg ccactgggag aggagctagt acagactctg     360

tacctcagga tctgggcaat ggaagagact ccggaatcct tgaagatcct ccaaatgagg     420

gaggatatcc gagatcaggt gctgaagatg aaaaccgaga gatggctgcg aaccctgata     480

agaggggaga agaccaagct gaaggacttc cagaagagat acgaagaagt gcacccctac     540

ctgatgaaag agaaggtaga gcagataata atggaagagg cgtggagcct ggcagcccac     600

atagtgcaag agtga                                                      615


<210> SEQ ID NO 10
<211> LENGTH: 204
<212> TYPE: PRT
<213> ORGANISM: Sendai virus

<400> SEQUENCE: 10
```

```
Met Pro Ser Phe Leu Lys Lys Ile Leu Lys Leu Arg Gly Arg Arg Gln
1               5                   10                  15

Glu Asp Glu Ser Arg Ser Arg Met Leu Ser Asp Ser Ser Thr Gln Ser
            20                  25                  30

Tyr Gln Val Asn Gln Leu Thr Ser Glu Gly Thr Glu Ala Gly Ser Thr
        35                  40                  45

Ile Pro Ser Thr Pro Ser Lys Gly Gln Ala Leu Pro Thr Glu Ser Lys
    50                  55                  60

Val Arg Ala Arg Glu Lys Ser Arg His Arg Arg Pro Lys Ile Ile Asp
65                  70                  75                  80

Gln Val Arg Arg Val Glu Ser Leu Gly Glu Gln Ala Ser Gln Arg Gln
                85                  90                  95

Lys His Met Leu Glu Thr Leu Ile Asn Lys Ile Tyr Thr Gly Pro Leu
            100                 105                 110

Gly Glu Glu Leu Val Gln Thr Leu Tyr Leu Arg Ile Trp Ala Met Glu
        115                 120                 125

Glu Thr Pro Glu Ser Leu Lys Ile Leu Gln Met Arg Glu Asp Ile Arg
    130                 135                 140

Asp Gln Val Leu Lys Met Lys Thr Glu Arg Trp Leu Arg Thr Leu Ile
145                 150                 155                 160

Arg Gly Glu Lys Thr Lys Leu Lys Asp Phe Gln Lys Arg Tyr Glu Glu
                165                 170                 175

Val His Pro Tyr Leu Met Lys Glu Lys Val Glu Gln Ile Ile Met Glu
            180                 185                 190

Glu Ala Trp Ser Leu Ala Ala His Ile Val Gln Glu
        195                 200
```

<210> SEQ ID NO 11
<211> LENGTH: 1108
<212> TYPE: DNA
<213> ORGANISM: Sendai virus

<400> SEQUENCE: 11

```
tggatcaaga tgccctcatt tctaaagaag attctgaagt tgagagggag gcgtcaggag     60

gacgagagtc gctctcggat gttatcggat tcctcgacgc agtcctatca agtgaaccaa    120

ctgacatcgg aggggacaga agctggctcc acaataccat caacaccctc caaaggccag    180

gctctaccca cagagtcaaa ggtgagggcg agggagaagt ctcgacatcg tcgacccaag    240

ataatcgatc aggtgaggag agtagagtct ctgggggaac aagcgagcca gaggcagaag    300

cacatgctag aaacgttgat aaacaaaata tacactgggc cactgggaga ggagctagta    360

cagactctgt acctcaggat ctgggcaatg gaagagactc cggaatcctt gaagatcctc    420

caaatgaggg aggatatccg agatcaggtg ctgaagatga aaccgagag atggctgcga     480

accctgataa gaggggagaa gaccaagctg aaggacttcc agaagagata cgaagaagtg    540

cacccctacc tgatgaaaga gaaggtagag cagataataa tggaagaggc gtggagcctg    600

gcagcccaca tagtgcaaga gtgactggag tcttggtgat ccccagtcct gagctcgaag    660

aggccgtgct acaaaggaac aagagacgac ccgccaacag cgggtccaga tctctcaccc    720

cagtggtcgt gcctagcact cggtctccac caccggacca tgacaatagt acaaggtcac    780

caccaaggaa acccccaacc acgcaggatg agcacaccaa ccccaggaac acccccgccg    840

tcaggatcaa ggatcggaga cccccaacag ggactcgctc cgccccagac cgcccgaccg    900

acggctatcc aacccaccca agtccagaga ccgatgcaac aaaaaagggc atagaagaga    960
```

```
acacatcatc tatgaaagag atggctacat tgttaacgag tcttggtgta atccagtctg   1020

ctcaagaatt cgagtcgtcc cgagacgcga gttatgtgtt tgcaaagcgt gccctaaaat   1080

ctgcaaacta tgcagagatg gcatttaa                                      1108


<210> SEQ ID NO 12
<211> LENGTH: 369
<212> TYPE: PRT
<213> ORGANISM: Sendai virus

<400> SEQUENCE: 12

Met Asp Gln Asp Ala Leu Ile Ser Lys Glu Asp Ser Glu Val Glu Arg
1               5                   10                  15

Glu Ala Ser Gly Gly Arg Glu Ser Leu Ser Asp Val Ile Gly Phe Leu
            20                  25                  30

Asp Ala Val Leu Ser Ser Glu Pro Thr Asp Ile Gly Gly Asp Arg Ser
        35                  40                  45

Trp Leu His Asn Thr Ile Asn Thr Leu Gln Arg Pro Gly Ser Thr His
    50                  55                  60

Arg Ala Lys Gly Glu Gly Glu Gly Glu Val Ser Thr Ser Ser Thr Gln
65                  70                  75                  80

Asp Asn Arg Ser Gly Glu Glu Ser Arg Val Ser Gly Gly Thr Ser Glu
                85                  90                  95

Pro Glu Ala Glu Ala His Ala Arg Asn Val Asp Lys Gln Asn Ile His
            100                 105                 110

Trp Ala Thr Gly Arg Gly Ala Ser Thr Asp Ser Val Pro Gln Asp Leu
        115                 120                 125

Gly Asn Gly Arg Asp Ser Gly Ile Leu Glu Asp Pro Pro Asn Glu Gly
    130                 135                 140

Gly Tyr Pro Arg Ser Gly Ala Glu Asp Glu Asn Arg Glu Met Ala Ala
145                 150                 155                 160

Asn Pro Asp Lys Arg Gly Glu Asp Gln Ala Glu Gly Leu Pro Glu Glu
                165                 170                 175

Ile Arg Arg Ser Ala Pro Leu Pro Asp Glu Gly Glu Gly Arg Ala Asp
            180                 185                 190

Asn Asn Gly Arg Gly Val Glu Ser Gly Ser Pro His Ser Ala Arg Val
        195                 200                 205

Thr Gly Val Leu Val Ile Pro Ser Pro Glu Leu Glu Glu Ala Val Leu
    210                 215                 220

Gln Arg Asn Lys Arg Arg Pro Ala Asn Ser Gly Ser Arg Ser Leu Thr
225                 230                 235                 240

Pro Val Val Val Pro Ser Thr Arg Ser Pro Pro Pro Asp His Asp Asn
                245                 250                 255

Ser Thr Arg Ser Pro Pro Arg Lys Pro Pro Thr Thr Gln Asp Glu His
            260                 265                 270

Thr Asn Pro Arg Asn Thr Pro Ala Val Arg Ile Lys Asp Arg Arg Pro
        275                 280                 285

Pro Thr Gly Thr Arg Ser Ala Pro Asp Arg Pro Thr Asp Gly Tyr Pro
    290                 295                 300

Thr His Pro Gly Pro Glu Thr Asp Ala Thr Lys Lys Gly His Arg Arg
305                 310                 315                 320

Glu His Ile Ile Tyr Glu Arg Asp Gly Tyr Ile Val Asn Glu Ser Trp
                325                 330                 335

Cys Asn Pro Val Cys Ser Arg Ile Arg Val Ile Ser Arg Arg Glu Leu
```

```
            340                 345                 350

Cys Val Cys Lys Ala Cys Pro Lys Ile Cys Lys Leu Cys Arg Asp Asp
        355                 360                 365

Ile
```

<210> SEQ ID NO 13
<211> LENGTH: 955
<212> TYPE: DNA
<213> ORGANISM: Sendai virus
<220> FEATURE:
<223> OTHER INFORMATION: This is a combined DNA/RNA sequence.

<400> SEQUENCE: 13

```
atggatcaag atgccttcat tcttaaagaa gattctgaag ttgagaggga ggcgccagga      60

ggaagagagt cgctctcgga tgttatcgga ttcctcgatg ctgtcctgtc gagtgaacca     120

actgacatcg gaggggacag gagctggctc cacaacacca tcaacactcc ccaaggacca     180

ggctctgccc atagagccaa aagtgagggc gaaggagaag tctcaacacc gtcgacccaa     240

gataatcgat caggtgagga gagtagagtc tctgggagaa caagcaagcc agaggcagaa     300

gcacatgctg gaaaccttga taaacaaaat atacaccggg cctttggggg aagaactggt     360

acaaactctg tatctcagga tctgggcgat ggaggagact ccggaatcct tgaaaatcct     420

ccaaatgaga gaggatatcc gagatcaggt attgaagatg aaaacagaga gatggctgcg     480

caccctgata agaggggaga agaccaagct gaaggacttc cagaagaggt acgaggaggt     540

acatccctac ctgatgaagg agaaggtgga gcaagtaata atggaagaag catggagcct     600

ggcagctcac atagtgcaag agtaactggg gtcctggtga ttcctagccc cgaactcgaa     660

gaggctgtgc tacggaggaa caaaagaaga cctaccaaca gtgggtccaa acctcttact     720

ccagcaaccg tgcctggcac ccggtcccca ccgctgaatc gttacaacag cacagggtca     780

ccaccaggaa aacccccatc tacacaggat gagcacatca actctgggga caccccccgcc     840

gtcagggtca aagaccggaa accaccaata gggacccgct ctgtctcaga ttgtccagcc     900

aacggccgcc caatccaccc gggtctagag accgactcaa caaaaaaggg catag          955
```

<210> SEQ ID NO 14
<211> LENGTH: 318
<212> TYPE: PRT
<213> ORGANISM: Sendai virus

<400> SEQUENCE: 14

```
Met Asp Gln Asp Ala Phe Ile Leu Lys Glu Asp Ser Glu Val Glu Arg
1               5                   10                  15

Glu Ala Pro Gly Gly Arg Glu Ser Leu Ser Asp Val Ile Gly Phe Leu
            20                  25                  30

Asp Ala Val Leu Ser Ser Glu Pro Thr Asp Ile Gly Gly Asp Arg Ser
        35                  40                  45

Trp Leu His Asn Thr Ile Asn Thr Pro Gln Gly Pro Gly Ser Ala His
    50                  55                  60

Arg Ala Lys Ser Glu Gly Glu Gly Glu Val Ser Thr Pro Ser Thr Gln
65                  70                  75                  80

Asp Asn Arg Ser Gly Glu Glu Ser Arg Val Ser Gly Arg Thr Ser Lys
                85                  90                  95

Pro Glu Ala Glu Ala His Ala Gly Asn Leu Asp Lys Gln Asn Ile His
            100                 105                 110

Arg Ala Phe Gly Gly Arg Thr Gly Thr Asn Ser Val Ser Gln Asp Leu
```

```
        115                 120                 125

Gly Asp Gly Gly Asp Ser Gly Ile Leu Glu Asn Pro Pro Asn Glu Arg
    130                 135                 140

Gly Tyr Pro Arg Ser Gly Ile Glu Asp Glu Asn Arg Glu Met Ala Ala
145                 150                 155                 160

His Pro Asp Lys Arg Gly Glu Asp Gln Ala Glu Gly Leu Pro Glu Glu
                165                 170                 175

Val Arg Gly Gly Thr Ser Leu Pro Asp Glu Gly Glu Gly Gly Ala Ser
            180                 185                 190

Asn Asn Gly Arg Ser Met Glu Pro Gly Ser Ser His Ser Ala Arg Val
        195                 200                 205

Thr Gly Val Leu Val Ile Pro Ser Pro Glu Leu Glu Glu Ala Val Leu
    210                 215                 220

Arg Arg Asn Lys Arg Arg Pro Thr Asn Ser Gly Ser Lys Pro Leu Thr
225                 230                 235                 240

Pro Ala Thr Val Pro Gly Thr Arg Ser Pro Pro Leu Asn Arg Tyr Asn
                245                 250                 255

Ser Thr Gly Ser Pro Pro Gly Lys Pro Pro Ser Thr Gln Asp Glu His
            260                 265                 270

Ile Asn Ser Gly Asp Thr Pro Ala Val Arg Val Lys Asp Arg Lys Pro
        275                 280                 285

Pro Ile Gly Thr Arg Ser Val Ser Asp Cys Pro Ala Asn Gly Arg Pro
    290                 295                 300

Ile His Pro Gly Leu Glu Thr Asp Ser Thr Lys Lys Gly Ile
305                 310                 315
```

<210> SEQ ID NO 15
<211> LENGTH: 546
<212> TYPE: DNA
<213> ORGANISM: Sendai virus
<220> FEATURE:
<223> OTHER INFORMATION: This is a combined DNA/RNA sequence.

<400> SEQUENCE: 15

```
atgttatcgg attcctcgac gcagtcctat caagtgaacc aactgacatc ggaggggaca     60

gaagctggct ccacaatacc atcaacaccc tccaaaggcc aggctctacc cacagagtca    120

aaggtgaggg cgagggagaa gtctcgacat cgtcgaccca agataatcga tcaggtgagg    180

agagtagagt ctctgggga acaagcgagc cagaggcaga agcacatgct agaaacgttg    240

ataaacaaaa tatacactgg gccactggga gaggagctag tacagactct gtacctcagg    300

atctgggcaa tggaagagac tccggaatcc ttgaagatcc tccaaatgag ggaggatatc    360

cgagatcagg tgctgaagat gaaaaccgag agatggctgc gaaccctgat aagaggggag    420

aagaccaagc tgaaggactt ccagaagaga tacgaagaag tgcaccccta cctgatgaaa    480

gagaaggtag agcagataat aatggaagag gcgtggagcc tggcagccca catagtgcaa    540

gagtga                                                               546
```

<210> SEQ ID NO 16
<211> LENGTH: 181
<212> TYPE: PRT
<213> ORGANISM: Sendai virus

<400> SEQUENCE: 16

```
Met Leu Ser Asp Ser Ser Thr Gln Ser Tyr Gln Val Asn Gln Leu Thr
1               5                   10                  15
```

```
Ser Glu Gly Thr Glu Ala Gly Ser Thr Ile Pro Ser Thr Pro Ser Lys
            20                  25                  30

Gly Gln Ala Leu Pro Thr Glu Ser Lys Val Arg Ala Arg Glu Lys Ser
        35                  40                  45

Arg His Arg Arg Pro Lys Ile Ile Asp Gln Val Arg Arg Val Glu Ser
    50                  55                  60

Leu Gly Glu Gln Ala Ser Gln Arg Gln Lys His Met Leu Glu Thr Leu
65                  70                  75                  80

Ile Asn Lys Ile Tyr Thr Gly Pro Leu Gly Glu Glu Leu Val Gln Thr
                85                  90                  95

Leu Tyr Leu Arg Ile Trp Ala Met Glu Glu Thr Pro Glu Ser Leu Lys
            100                 105                 110

Ile Leu Gln Met Arg Glu Asp Ile Arg Asp Gln Val Leu Lys Met Lys
        115                 120                 125

Thr Glu Arg Trp Leu Arg Thr Leu Ile Arg Gly Glu Lys Thr Lys Leu
    130                 135                 140

Lys Asp Phe Gln Lys Arg Tyr Glu Glu Val His Pro Tyr Leu Met Lys
145                 150                 155                 160

Glu Lys Val Glu Gln Ile Ile Met Glu Glu Ala Trp Ser Leu Ala Ala
                165                 170                 175

His Ile Val Gln Glu
            180


<210> SEQ ID NO 17
<211> LENGTH: 528
<212> TYPE: PRT
<213> ORGANISM: Sendai virus

<400> SEQUENCE: 17

Ala Thr Gly Cys Thr Gly Thr Cys Cys Thr Gly Thr Cys Gly Ala Gly
1               5                   10                  15

Thr Gly Ala Ala Cys Cys Ala Ala Cys Thr Gly Ala Cys Ala Thr Cys
            20                  25                  30

Gly Gly Ala Gly Gly Gly Gly Ala Cys Ala Gly Ala Ala Gly Cys Thr
        35                  40                  45

Gly Gly Cys Thr Cys Cys Ala Cys Ala Ala Cys Ala Cys Cys Ala Thr
    50                  55                  60

Cys Ala Ala Cys Ala Cys Thr Cys Cys Cys Cys Ala Ala Gly Gly Ala
65                  70                  75                  80

Cys Cys Ala Gly Gly Cys Thr Cys Thr Gly Cys Cys Cys Ala Thr Ala
                85                  90                  95

Gly Ala Gly Cys Cys Ala Ala Ala Ala Gly Thr Gly Ala Gly Gly Gly
            100                 105                 110

Cys Gly Ala Ala Gly Gly Ala Gly Ala Ala Gly Thr Cys Thr Cys Ala
        115                 120                 125

Ala Cys Ala Cys Cys Gly Thr Cys Gly Ala Cys Cys Cys Ala Ala Gly
    130                 135                 140

Ala Thr Ala Ala Thr Cys Gly Ala Thr Cys Ala Gly Gly Thr Gly Ala
145                 150                 155                 160

Gly Gly Ala Gly Ala Gly Thr Ala Gly Ala Gly Thr Cys Thr Cys Thr
                165                 170                 175

Gly Gly Gly Ala Gly Ala Ala Cys Ala Ala Gly Cys Ala Ala Gly Cys
            180                 185                 190

Cys Ala Gly Ala Gly Gly Cys Ala Gly Ala Ala Gly Cys Ala Cys Ala
        195                 200                 205
```

```
Thr Gly Cys Thr Gly Gly Ala Ala Ala Cys Cys Thr Thr Gly Ala Thr
    210                 215                 220

Ala Ala Ala Cys Ala Ala Ala Ala Thr Ala Thr Ala Cys Ala Cys Cys
225                 230                 235                 240

Gly Gly Gly Cys Cys Thr Thr Thr Gly Gly Gly Gly Gly Ala Ala Gly
                245                 250                 255

Ala Ala Cys Thr Gly Gly Thr Ala Cys Ala Ala Ala Cys Thr Cys Thr
            260                 265                 270

Gly Thr Ala Thr Cys Thr Cys Ala Gly Gly Ala Thr Cys Thr Gly Gly
        275                 280                 285

Gly Cys Gly Ala Thr Gly Gly Ala Gly Gly Ala Gly Ala Cys Thr Cys
    290                 295                 300

Cys Gly Gly Ala Ala Thr Cys Cys Thr Thr Gly Ala Ala Ala Ala Thr
305                 310                 315                 320

Cys Cys Thr Cys Cys Ala Ala Ala Thr Gly Ala Gly Ala Gly Ala Gly
                325                 330                 335

Gly Ala Thr Ala Thr Cys Cys Gly Ala Gly Ala Thr Cys Ala Gly Gly
            340                 345                 350

Thr Ala Thr Thr Gly Ala Ala Gly Ala Thr Gly Ala Ala Ala Ala Cys
        355                 360                 365

Ala Gly Ala Gly Ala Gly Ala Thr Gly Gly Cys Thr Gly Cys Gly Cys
    370                 375                 380

Ala Cys Cys Cys Thr Gly Ala Thr Ala Ala Gly Ala Gly Gly Gly Gly
385                 390                 395                 400

Ala Gly Ala Ala Gly Ala Cys Cys Ala Ala Gly Cys Thr Gly Ala Ala
                405                 410                 415

Gly Gly Ala Cys Thr Thr Cys Cys Ala Gly Ala Ala Gly Ala Gly Gly
            420                 425                 430

Thr Ala Cys Gly Ala Gly Gly Ala Gly Gly Thr Ala Cys Ala Thr Cys
        435                 440                 445

Cys Cys Thr Ala Cys Cys Thr Gly Ala Thr Gly Ala Ala Gly Gly Ala
    450                 455                 460

Gly Ala Ala Gly Gly Thr Gly Gly Ala Gly Cys Ala Ala Gly Thr Ala
465                 470                 475                 480

Ala Thr Ala Ala Thr Gly Gly Ala Ala Gly Ala Ala Gly Cys Ala Thr
                485                 490                 495

Gly Gly Ala Gly Cys Cys Thr Gly Gly Cys Ala Gly Cys Thr Cys Ala
            500                 505                 510

Cys Ala Thr Ala Gly Thr Gly Cys Ala Ala Gly Ala Gly Thr Ala Ala
        515                 520                 525
```

<210> SEQ ID NO 18
<211> LENGTH: 175
<212> TYPE: PRT
<213> ORGANISM: Sendai virus

<400> SEQUENCE: 18

```
Met Leu Ser Cys Arg Val Asn Gln Leu Thr Ser Glu Gly Thr Glu Ala
1               5                   10                  15

Gly Ser Thr Thr Pro Ser Thr Leu Pro Lys Asp Gln Ala Leu Pro Ile
            20                  25                  30

Glu Pro Lys Val Arg Ala Lys Glu Lys Ser Gln His Arg Arg Pro Lys
        35                  40                  45

Ile Ile Asp Gln Val Arg Arg Val Glu Ser Leu Gly Glu Gln Ala Ser
```

```
    50                  55                  60

Gln Arg Gln Lys His Met Leu Glu Thr Leu Ile Asn Lys Ile Tyr Thr
65                  70                  75                  80

Gly Pro Leu Gly Glu Glu Leu Val Gln Thr Leu Tyr Leu Arg Ile Trp
                85                  90                  95

Ala Met Glu Glu Thr Pro Glu Ser Leu Lys Ile Leu Gln Met Arg Glu
            100                 105                 110

Asp Ile Arg Asp Gln Val Leu Lys Met Lys Thr Glu Arg Trp Leu Arg
        115                 120                 125

Thr Leu Ile Arg Gly Glu Lys Thr Lys Leu Lys Asp Phe Gln Lys Arg
    130                 135                 140

Tyr Glu Glu Val His Pro Tyr Leu Met Lys Glu Lys Val Glu Gln Val
145                 150                 155                 160

Ile Met Glu Glu Ala Trp Ser Leu Ala Ala His Ile Val Gln Glu
                165                 170                 175


<210> SEQ ID NO 19
<211> LENGTH: 1730
<212> TYPE: DNA
<213> ORGANISM: Artificial sequence
<220> FEATURE:
<223> OTHER INFORMATION: cloning region of pSL1180
<220> FEATURE:
<223> OTHER INFORMATION: This is a combined DNA/RNA sequence.

<400> SEQUENCE: 19

acggcttcgg ctacacttac cgcatggatc aagatgcctt cattcttaaa gaagattctg     60

aagttgagag ggaggcgcca ggaggaagag agtcgctctc ggatgttatc ggattcctcg    120

atgctgtcct gtcgagtgaa ccaactgaca tcggaggggga cagaagctgg ctccacaaca    180

ccatcaacac tccccaagga ccaggctctg cccatagagc caaaagtgag ggcgaaggag    240

aagtctcaac accgtcgacc caagataatc gatcaggtga ggagagtaga gtctctggga    300

gaacaagcaa gccagaggca gaagcacatg ctggaaacct tgataaacaa aatatacacc    360

gggcctttgg gggaagaact ggtacaaact ctgtatctca ggatctgggc gatggaggag    420

actccggaat ccttgaaaat cctccaaatg agagaggata tccgagatca ggtattgaag    480

atgaaaacag agagatggct gcgcaccctg ataagagggg agaagaccaa gctgaaggac    540

ttccagaaga ggtacgagga ggtacatccc tacctgatga aggagaaggt ggagcaagta    600

ataatggaag aagcatggag cctggcagct cacatagtgc aagagtaact ggggtcctgg    660

tgattcctag ccccgaactc gaagaggctg tgctacggag gaacaaaaga agacctacca    720

acagtgggtc caaacctctt actccagcaa ccgtgcctgg cacccggtcc ccaccgctga    780

atcgttacaa cagcacaggg tcaccaccag gaaaaccccc atctacacag gatgagcaca    840

tcaactctgg ggacaccccc gccgtcaggg tcaaagaccg gaaaccacca atagggaccc    900

gctctgtctc agattgtcca gccaacggcc gcccaatcca cccgggtcta gagaccgact    960

caacaaaaaa gggcatagga gagaacacat catctatgaa agagatggct acattgttga   1020

cgagtcttgg tgtaatccag tctgctcaag aattcgagtc atcccgagac gcgagttatg   1080

tgtttgcaag acgtgcccta aagtctgcaa actatgcaga gatgacattc aatgtatgcg   1140

gcctgatcct ttctgccgag aaatcttccg ctcgtaaggt agatgagaac aaacaactgc   1200

tcaaacagat ccaagagagc gtggaatcat tccgggatat ttacaagaga ttctctgagt   1260

atcagaaaga acagaactca ttgctgatgt ccaacctatc tacacttcat atcatcacag   1320
```

```
atagaggtgg caagactgac aacacagact cccttacaag gtccccctcc gtttttgcaa   1380

aatcaaaaga gaacaagact aaggctacca ggtttgaccc atctatggag accctagaag   1440

atatgaagta caaaccggac ctaatccgag aggatgaatt tagagatgag atccgcaacc   1500

cggtgtacca agagagggac acagaaccca gggcctcaaa cgcatcacgc ctcctcccct   1560

ccaaagagaa gcccacaatg cactctctca ggctcgtcat agagagcagt cccctaagca   1620

gagctgagaa agcagcatat gtgaaatcat tatccaagtg caagacagac caagaggtta   1680

aggcagtcat ggaactcgta gaagaggaca tagagtcact gaccaactag              1730


<210> SEQ ID NO 20
<211> LENGTH: 51
<212> TYPE: DNA
<213> ORGANISM: Artificial sequence
<220> FEATURE:
<223> OTHER INFORMATION: PCR primer 1
<220> FEATURE:
<223> OTHER INFORMATION: This is a combined DNA/RNA sequence.

<400> SEQUENCE: 20

cgcatggatc aagacgcctt cattctaaaa gaagattctg aagtagagag g              51


<210> SEQ ID NO 21
<211> LENGTH: 51
<212> TYPE: DNA
<213> ORGANISM: Artificial sequence
<220> FEATURE:
<223> OTHER INFORMATION: P gene
<220> FEATURE:
<223> OTHER INFORMATION: This is a combined DNA/RNA sequence.

<400> SEQUENCE: 21

cgcatggatc aagatgcctt cattcttaaa gaagattctg aagttgagag g              51


<210> SEQ ID NO 22
<211> LENGTH: 51
<212> TYPE: DNA
<213> ORGANISM: Artificial sequence
<220> FEATURE:
<223> OTHER INFORMATION: P gene mut.
<220> FEATURE:
<223> OTHER INFORMATION: This is a combined DNA/RNA sequence.

<400> SEQUENCE: 22

cgcatggatc aagacgcctt cattctaaaa gaagattctg aagtagagag g              51


<210> SEQ ID NO 23
<211> LENGTH: 38
<212> TYPE: DNA
<213> ORGANISM: Artificial sequence
<220> FEATURE:
<223> OTHER INFORMATION: C gene mut.
<220> FEATURE:
<223> OTHER INFORMATION: This is a combined DNA/RNA sequence.

<400> SEQUENCE: 23

acgccttcat tctaaaagaa gattctgaag tagagagg                             38


<210> SEQ ID NO 24
<211> LENGTH: 36
<212> TYPE: DNA
<213> ORGANISM: Artificial sequence
<220> FEATURE:
<223> OTHER INFORMATION: PCR primer 2
<220> FEATURE:
<223> OTHER INFORMATION: This is a combined DNA/RNA sequence.
```

<400> SEQUENCE: 24
ctctcggacg ttatcggatt cctcgacgct gtcctg 36

<210> SEQ ID NO 25
<211> LENGTH: 36
<212> TYPE: DNA
<213> ORGANISM: Artificial sequence
<220> FEATURE:
<223> OTHER INFORMATION: P gene
<220> FEATURE:
<223> OTHER INFORMATION: This is a combined DNA/RNA sequence.

<400> SEQUENCE: 25
ctctcggacg ttatcggatt cctcgacgct gtcctg 36

<210> SEQ ID NO 26
<211> LENGTH: 36
<212> TYPE: DNA
<213> ORGANISM: Artificial sequence
<220> FEATURE:
<223> OTHER INFORMATION: Y1 gene
<220> FEATURE:
<223> OTHER INFORMATION: This is a combined DNA/RNA sequence.

<400> SEQUENCE: 26
ctctcggatg ttatcggatt cctcgatgct gtcctg 36

<210> SEQ ID NO 27
<211> LENGTH: 36
<212> TYPE: DNA
<213> ORGANISM: Artificial sequence
<220> FEATURE:
<223> OTHER INFORMATION: Y1 gene mut.
<220> FEATURE:
<223> OTHER INFORMATION: This is a combined DNA/RNA sequence.

<400> SEQUENCE: 27
ctctcggacg ttatcggatt cctcgacgct gtcctg 36

<210> SEQ ID NO 28
<211> LENGTH: 42
<212> TYPE: DNA
<213> ORGANISM: Artificial sequence
<220> FEATURE:
<223> OTHER INFORMATION: PCR primer 3
<220> FEATURE:
<223> OTHER INFORMATION: This is a combined DNA/RNA sequence.

<400> SEQUENCE: 28
gactcaacaa agaaaggcat aggtgagaac acatcatcta tg 42

<210> SEQ ID NO 29
<211> LENGTH: 42
<212> TYPE: DNA
<213> ORGANISM: Artificial sequence
<220> FEATURE:
<223> OTHER INFORMATION: P gene
<220> FEATURE:
<223> OTHER INFORMATION: This is a combined DNA/RNA sequence.

<400> SEQUENCE: 29
gactcaacaa aaaagggcat aggagagaac acatcatcta tg 42

<210> SEQ ID NO 30
<211> LENGTH: 42
<212> TYPE: DNA

```
<213> ORGANISM: Artificial sequence
<220> FEATURE:
<223> OTHER INFORMATION: P gene mut.
<220> FEATURE:
<223> OTHER INFORMATION: This is a combined DNA/RNA sequence.

<400> SEQUENCE: 30

gactcaacaa agaaaggcat aggtgagaac acatcatcta tg                        42


<210> SEQ ID NO 31
<211> LENGTH: 43
<212> TYPE: DNA
<213> ORGANISM: Artificial sequence
<220> FEATURE:
<223> OTHER INFORMATION: V gene mut.
<220> FEATURE:
<223> OTHER INFORMATION: This is a combined DNA/RNA sequence.

<400> SEQUENCE: 31

gactcaacaa agaaagggca taggtgagaa cacatcatct atg                       43


<210> SEQ ID NO 32
<211> LENGTH: 44
<212> TYPE: DNA
<213> ORGANISM: Artificial sequence
<220> FEATURE:
<223> OTHER INFORMATION: W gene mut.
<220> FEATURE:
<223> OTHER INFORMATION: This is a combined DNA/RNA sequence.

<400> SEQUENCE: 32

gactcaacaa agaaaggggc ataggtgaga acacatcatc tatg                      44


<210> SEQ ID NO 33
<211> LENGTH: 15
<212> TYPE: DNA
<213> ORGANISM: Artificial sequence
<220> FEATURE:
<223> OTHER INFORMATION: cleavage site in the F gene of SeV
<220> FEATURE:
<223> OTHER INFORMATION: This is a combined DNA/RNA sequence.

<400> SEQUENCE: 33

gttccacagt cgaga                                                      15


<210> SEQ ID NO 34
<211> LENGTH: 15
<212> TYPE: DNA
<213> ORGANISM: Artificial Sequence
<220> FEATURE:
<223> OTHER INFORMATION: cleavage site in the F gene of NDV
<220> FEATURE:
<223> OTHER INFORMATION: This is a combined DNA/RNA sequence.

<400> SEQUENCE: 34

cgtcgtcaga agagg                                                      15


<210> SEQ ID NO 35
<211> LENGTH: 4
<212> TYPE: PRT
<213> ORGANISM: Artificial Sequence
<220> FEATURE:
<223> OTHER INFORMATION: Urokinase-type plasminogen activator (uPa)
      sensitive consensus target site

<400> SEQUENCE: 35

Ser Gly Arg Ser
1
```

```
<210> SEQ ID NO 36
<211> LENGTH: 7
<212> TYPE: PRT
<213> ORGANISM: Artificial Sequence
<220> FEATURE:
<223> OTHER INFORMATION: Mutation to SeV P protein sequence

<400> SEQUENCE: 36

Lys Lys Gly His Arg Arg Glu
1               5


<210> SEQ ID NO 37
<211> LENGTH: 5
<212> TYPE: PRT
<213> ORGANISM: Artificial Sequence
<220> FEATURE:
<223> OTHER INFORMATION: Mutation to SeV P protein sequence (modified V
      sequence)

<400> SEQUENCE: 37

Lys Lys Gly His Arg
1               5


<210> SEQ ID NO 38
<211> LENGTH: 4
<212> TYPE: PRT
<213> ORGANISM: Artificial Sequence
<220> FEATURE:
<223> OTHER INFORMATION: Mutation to SeV P protein sequence (unmodified
      W sequence)

<400> SEQUENCE: 38

Lys Lys Gly Ala
1


<210> SEQ ID NO 39
<211> LENGTH: 21
<212> TYPE: DNA
<213> ORGANISM: Sendai virus
<220> FEATURE:
<223> OTHER INFORMATION: This is a combined DNA/RNA sequence.

<400> SEQUENCE: 39

acaaaaaagg gcataggaga g                                               21
```

GENETICALLY MODIFIED PARAMYXOVIRUS FOR TREATMENT OF TUMOR DISEASES

CROSS-REFERENCE TO RELATED APPLICATIONS

This application is a continuation of copending international patent application PCT/EP2011/056290 filed on 20 Apr. 2011 and designating the U.S., which has been published in German, and claims priority from German patent application DE 10 2010 018 961.8 filed on 23 Apr. 2010. The entire contents of these prior applications are incorporated herein by reference.

REFERENCE TO A SEQUENCE LISTING

This application contains references to amino acid sequences and/or nucleic acid sequences which have been submitted concurrently herewith as the sequence listing text file "17955859_1.txt", file size 44 KiloBytes (KB), created on 20 Aug. 2013. The aforementioned sequence listing is hereby incorporated by reference in its entirety pursuant to 37 C.F.R. §1.52(e)(5). The substitute sequence listing in the ASCII text file entitled "5402P453-US.txt" is hereby incorporated by reference in its entirety. The ASCII text file entitled "5402P453-US.txt" was created on 4 Dec. 2012 and the size is 45 KB.

FIELD

The present invention relates to a genetically modified Paramyxovirus, a pharmaceutical composition comprising this Paramyxovirus, the use of a genetically modified Paramyxovirus for the therapeutic and/or prophylactic treatment of a tumor disease, and a method for the production of a pharmaceutical composition for the therapeutic or prophylactic treatment of a tumor disease.

BACKGROUND

Statistically, every third European develops cancer in his lifetime. In Germany every year about 395,000 human beings develop cancer, about 195,000 thereof are women and 200,000 are men. Most of these cases develop at the age of over 60 years.

Solid tumors are still a big challenge of the clinical oncology. A significant improvement of the prognosis of individual tumor diseases can almost exclusively be reached by establishing new principles of therapy, integrated into multimodal concepts.

One of these new principles of therapy relates to the application of replicating viruses for the treatment of tumors. This approach is referred to as virotherapy or oncolysis. Numerous viruses have oncolytic properties with a preferred replication in different tumor cells in comparison to a reduced replication in healthy parenchyma cells. Currently, multiple virotherapeutic agents are subject of several clinical trials.

Viruses of the family of Paramyxoviridae are of particular interest. Important members of this family of enveloped viruses are the Newcastle disease virus which belongs to the genus of *Avulavirus*, the Measles virus which belongs to the genus of *Morbilliviruses*, and the Sendai virus belonging to the genus of the *Respiroviruses*.

The genome of the Paramyxoviruses comprises a negative single-stranded RNA, i.e. an RNA molecule encoding genes or open reading frames (ORFs) in the anti-sense mode. In a Sendai virus the 3'-head region of the RNA genome is followed by the viral genes N (Nucleocapsid), P (Phospho), M (Matrix), F (Fusion), HN (Hemagglutinin-Neuraminidase) and L (Large), followed by the 5'-tail region.

The N, P, and L proteins are required for the expression of the genes encoded by the genomic RNA and for the autonomous replication of the RNA. The HN protein supports the infection of specific cell types. The so-called Matrix protein (M) is a structure protein in the virus particle which is associated with the membrane.

The F protein has a central function in the infection by inducing the cell membran fusion which is necessary for the initial infection and the virus expansion to the neighboring cells. It is synthesized in virus-infected cells as an inactive precursor F0 and anchored in the lipid envelope of the virus which originates from the plasma membrane of the host cell. F0 is cleaved into the active subunits F1 and F2 by the tryptase "Clara" which can be found in the respiratory tract of rats and mice and is secreted from the bronchial epithelium cells. F1 and F2 have the capability to fuse cell membranes, thereby initiating the infection of the host by the virus. Therefore, the cleavage of F0 is a decisive determinate for the infectiousness and pathogenity of the Sendai virus. The protease restriction is an important determinant by which the infection with the Sendai virus in mice is restricted to the respiratory tract and cannot result in a systemic infection.

Kinoh et al. (2004), Generation of a recombinant Sendai virus that is selectively activated and lyses human tumor cells expressing matrix metalloproteinses, Gene Ther. 11, p. 1137-1145, propose the use of a genetically modified Sendai virus for the treatment of tumor diseases. The principle of the genetic modification is the introduction of an artificial cleavage site into the viral F protein, which is recognized and can be cleaved by tumor-specific matrix metalloproteinases and, thereby, should enable a tumor-specific replication of the modified viruses. Furthermore, the known genetically modified Sendai virus comprises a deletion in the viral M protein resulting in an inhibition of the release of offspring viruses in such a way that an expansion of the virus is only possible by cell-to-cell contacts via fusion. This modified Sendai virus is also disclosed in EP 1 505 154.

Kinoh et al. (2009), Generation of optimized and urokinase-targeted oncolytic Sendai virus vectors applicable for various human malignancies, Gene Ther. 16, p. 392-403, reports a genetically modified Sendai virus having a truncation of amino acids in the viral F protein which should result in an increase of the fusion activity. Furthermore, the viral F protein comprises a so-called "Urokinase Type Plaminogen Activator (uPA) Sensitive Sequence" (SGRS, SEQ ID NO:35) by which a cleavage and activiation of F0 through tumor-specific proteases should extend the replication capacity of the viruses to a multitude of tumors.

Elankumaran et al. (2010), Type I Interferone sensitive recombinant Newcastle-Disease-Virus for oncolytic virotherapy, Journal of Virology, online publication, propose the use of recombinant Newcastle disease viruses (rNDV) as an anti-tumor agent which either comprise a mutation in the V protein and is referred to as "rBC-Edit", or a mutation in the F protein and is referred to as "rLaSota V.F.".

US 2009/0175826 reports using a recombinant Newcastle disease virus (rNDV) as an oncolytic agent, which comprises a transgene which should induce apoptosis in tumor cell lines.

The oncolytic viruses described in the art so far have not proven of value. A clinical application with a defined proof of effectiveness is still to be demonstrated. In particular, the oncolytic viruses so far used in the art have the disadvantage of also infecting and destroying non-tumor cells to an extended degree. On these grounds the oncolytic viruses used so far are unusable in a clinical application. In addition, it is not clear for which tumor diseases a good effect of individual virus systems can be reached. For this reason the oncolytic viruses used so far are not usable in clinical applications.

SUMMARY

Against this background an object underlying the present invention is to provide an improved oncolytic virus by means of which the disadvantages of the oncolytic viruses used so far could be largely avoided. In particular, such oncolytic viruses should be provided which can replicate in tumor cells and destroy the latter, however which replicate in non-tumor cells only in a strongly restricted fashion and, thereby, fulfill a sufficient epidemiological safety aspect.

This object is achieved by the provision of a genetically modified Paramyxovirus, preferably a genetically modified Sendai virus (SeV) which, in reference to the wild type (wt), comprises in its F gene at least a first genetic modification and in its P gene at least a second genetic modification.

DETAILED DESCRIPTION

Figure 1:
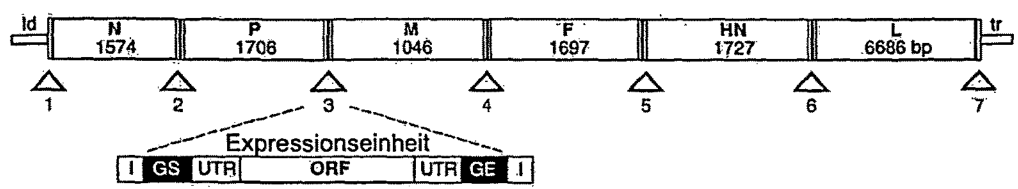
FIG. 1 shows the genomic structure of the Sendai virus.

As used herein, "Paramyxovirus" refers to such a virus which belongs to the family of Paramyxoviridae and a virus resulting therefrom by the way of propagation. Paramyxoviruses encompass the subfamily of Paramyxovirinae with the genera of Respiroviruses, Rubulaviruses, Avulaviruses, and Morbilliviruses as well as the subfamily of Pneumovirinae with the genera of Pneumoviruses, and Metapneumoviruses. Details on the taxonomy of the Paramyxoviruses can be found, for example in Kneipe et al. (2007), Fields Virology, 5th Edition, Lippincot Williams & Wilkins.

As the inventors were able to find out, basically every strain of the Sendai virus is qualified for the modification according to the invention. Especially suitable strains of the Sendai virus are "Fushimi", "Harris", "Z-Strain", "Ohita", "Hamamatsu", "Cantell", and "52".

The inventors have realized for the first time that a genetic modification of the F gene or the F protein, respectively, and the abolishment of the protease restriction provides for an efficient expansion of the virus in the tumor tissue so that a broad spectrum of different tumors can be infected.

The nucleotide sequence of the F gene of the Sendai virus is depicted in the enclosed sequence listing under SEQ ID NO: 1 and has the GeneID 1489775. The amino acid sequence of the F protein of the Sendai virus is depicted in the enclosed sequence listing under SEQ ID NO: 2 and has the database access nos. BAA 24390.1 or NP_056877.

The inventors have also realized that the second genetic modification in the P gene or P protein, respectively, results in an attenuation of the virus. Because of the genetic modification or mutation in the P gene, respectively, the reading frames for the genes or proteins C', C, Y1, Y2 are shifted. However, the P protein remains completely intact.

The nucleotide sequence of the P gene of the Sendai virus is depicted in the enclosed sequence listing under SEQ ID NO: 3. The amino acid sequence of the P protein is depicted in the enclosed sequence listing under SEQ ID NO: 4 and has the database access nos. BAA 24386.1 and AAB 06279.

The P gene encodes for several accessory non-structural proteins referred to as C', C, Y1, Y2, V and W. These proteins are generated by overlapping reading frames and "RNA editing". The exact functions of the accessory non-structural proteins are not fully illucidated in detail, whereas it is assumed that they can interact with the unspecific defense system of the infected cells, such as the interferon system.

The Paramyxoviruses as modified according to the invention are, in contrast to the wild type viruses, in the position to independently replicate in the tumor tissue and to destroy the latter, whereas no restriction to a specific tumor cell type can be observed. Surprisingly, the virus according to the invention can only replicate to a very limited extend in non-tumor cells, such as primary human hepatocytes or fibroblasts. As a result, the virus according to the invention infects tumor cells with a very high preference in reference to non-tumor cells. Damages of normal tissue are significantly reduced whereas the therapeutic scope of the virus is increased.

As used herein "genetic modification" refers to a preferably targeted alteration of the genome, the genetic information or the encoded proteins of the Paramyxovirus of the invention in reference to the wild type, which can e.g. be introduced by targeted mutagenesis.

In one embodiment the first genetic modification is designed in such a manner that it results in a tropism extension.

This measure has the advantage that the virus according to the invention becomes independent from specific proteases which e.g. are only expressed by a small number of tissues or tumor cells. In this context, for example the wild type Sendai virus depends on a tryptase which is only expressed by bronchial epithelium cells and, for this reason, it can only infect these cells. The virus described by Kinoh et al. (2009; I.c.) depends on the matrix metalloproteinase (MMP) and, therefore, can only infect such tumor cells which express MMP. In contrast, the further developed virus according to the invention is in the position to infect and lyse all tumor cells by reason of the first genetic modification in the F gene.

In another embodiment the second genetic modification is configured to result in a tropism restriction.

This measure has the advantage that the virus safety is increased and side effects are significantly reduced. The virus according to the invention selectively lyses tumor cells, however not healthy cells or only to a very limited extend. The inventors have realized that through the targeted genetic modification of a P gene, i.e. a non-structure protein, the mode of response of the cell to be lysed can be influenced in such a way that the virus replicates in tumor cells in a targeted manner. This approach differs from those described by Kinoh et al. (2009; I.c.) where a deletion of the M gene which encodes a structure protein, results in the synthesis of an incomplete virus particle. That also results in the reduction of the lysis activity. Surprisingly, the lysis activity of the virus according to the invention is, restricted to tumor cells, very high.

It is preferred if through the first genetic modification in the F gene that the nucleotide sequence encoding for the SeV WT protease cleavage site, which comprises the amino acid sequence VPQSR (SEQ ID NO: 5), is replaced by a nucleotide sequence encoding for a ubiquitous protease cleavage site, preferably from the F gene of the Newcastle disease virus (NDV), which comprises the amino acid sequence RRQKR (SEQ ID NO: 6).

The modification of the proteolytic SeV-WT protease cleavage site in the F protein according to the invention abolishes the protease restriction of the wild type. The F protein can then be cleaved by ubiquitous proteases by which an independency from specific proteases which might only be present in the respiratory tract of mice or also from tumor-reducing proteases can be reached. As a result, the genetically modified virus can be used for a broader spectrum of tumors, whereas the risk of the development of a resistance is significantly reduced.

In another embodiment the second genetic modification in the P gene results in a modification of an accessory non-structural protein encoded by the P gene, preferably in such a way that at least one of the latter is not transcribable, further preferred not transcribable because of a functional destruction of the start codon.

These measures have the advantage that the virus as modified according to the invention is attenuated in such a way that the replication in non-malign cells and the infection of healthy tissue is significantly restricted. Consequently the viruses according to the invention infect tumor cells in a more targeted manner and are capable to lyse them.

It is preferred if the accessory non-structural proteins are selected from the group consisting of: C', C, Y1, Y2, V and W, wherein it is preferred if through the second genetic modification in the P gene at least the C'/C and Y1/Y2 proteins, further preferred at least the C'/C, V, and W proteins, further preferred at least the C'/C, V, W and Y1/Y2 proteins are modified or functionally destructed, respectively.

As the inventors have been able to find out in a model system viruses which are modified in such a manner comprise a particularly high selectivity for tumor cells and a particularly poor replication capacity in non-tumor cells.

The nucleotide sequence of the C' gene of the Sendai virus is depicted in the enclosed sequence listing under SEQ ID NO: 7 and comprises the GeneID AB005796.1. The amino acid sequence of the C' protein of the Sendai virus is depicted in the enclosed sequence listing under SEQ ID NO: 8 and comprises the database access number BAA 24394.

The nucleotide sequence of the C gene of the Sendai virus is depicted in the enclosed sequence listing under SEQ ID NO: 9. The amino acid sequence of the C protein of the Sendai virus is depicted in the enclosed sequence listing under SEQ ID NO: 10 and has the database access number BAA 24396.

The nucleotide sequence of the V gene of the Sendai virus is depicted in the enclosed sequence listing under SEQ ID NO: 11. The amino acid sequence of the V protein of the Sendai virus is depicted in the enclosed sequence listing under SEQ ID NO: 12 and comprises the database access number BAA 20021.

The nucleotide sequence of the W gene of the Sendai virus is depicted in the enclosed sequence listing under SEQ ID NO: 13. The amino acid sequence of the W protein of the Sendai virus is depicted in the enclosed sequence listing under SEQ ID NO:14 and comprises the database access number AAX07444.

The nucleotide sequence of the Y1 gene of the Sendai virus is depicted in the enclosed sequence listing under SEQ ID NO: 15. The amino acid sequence of the Y1 protein of the Sendai virus is depicted in the enclosed sequence listing under SEQ ID NO: 16 and has the database access number BAA 24388.

The nucleotide sequence of the Y2 gene of the Sendai virus is depicted in the enclosed sequence listing under SEQ ID NO: 17. The amino acid sequence of the Y1 protein of the Sendai virus is depicted in the enclosed sequence listing under SEQ ID NO: 18 and has the data base access number AAX07449.

In another embodiment the virus according to the invention comprises, in reference to the wild type (wt), at least one transgene, preferably a suicide gene or other cell death inducing or immunostimulating genes.

This measure has the advantage that the cytotoxicity of the virus according to the invention is again increased as the product of the transgene additionally contributes to an intensified destruction of the infected tumor cells. Transgenes having an anti-tumor effect are also encompassed.

Against this background a further embodiment of the present invention is a pharmaceutical composition comprising the genetically modified Paramyxovirus according to the invention and a pharmaceutically acceptable carrier.

Pharmaceutically acceptable carriers are comprehensively described in the state of the art, for example in Bauer et al. (1999), Lehrbuch der Pharmazeutischen Technologie, Wissenschaftliche Verlagsgesellschaft mbH Stuttgart, Kibbe et al. (2000), Handbook of Pharmaceutical Excipients, American Pharmaceutical Association and Pharmaceutical Press. The content of the before-mentioned publications is subject of the present disclosure. It goes without saying that the pharmaceutical composition may comprise further accessory and active agents, such as cytostatics.

Another embodiment of the present invention is the use of the genetically modified paramyxovirus according to the invention for the therapeutic and/or prophylactic treatment of a tumor disease, preferably the development of a solid tumor, further preferred the development of a hepatocellular carcinoma.

The hepatocellular carcinoma has an incidence of one million each year and thus is worldwide one of the most frequent malignomas. Only in few cases a curative therapy is possible by means of resection and liver transplantation. So far convincing alternative concepts of therapy are lacking, since a distinct resistance against all chemotherapeutics tested so far can be observed. These needs are effectively met by the invention.

Another embodiment of the present invention is a method for the production of a pharmaceutical composition for the therapeutic and/or prophylactic treatment of a tumor disease, preferably the development of a solid tumor, further preferred the development of a hepatocellular carcinoma, comprising the following steps: (1) Providing the genetically modified Paramyxovirus according to the invention, and (2) formulating the genetically modified Paramyxovirus into a pharmaceutically acceptable carrier.

It is to be understood that the features mentioned before and those to be explained in the following cannot only be used in the combination as specifically indicated but also in other combinations or in isolated manner without departing from the scope of the invention.

The present invention will now be explained by means of embodiments resulting in further features, advantages and characteristics of the invention. Reference is made to the enclosed figures.

EXAMPLES

1. Genomic Organisation of the Sendai Viruses

Sendai viruses are negative strand RNA viruses with a genome of approximately 15 kb. The genomic organization is shown in FIG. 1. The genes of the six structure proteins are arranged on the viral genomic RNA having the order of 3'-N-P-M-F-HN-L-5'. In front of the first gene the leader region (Id) encompassing 54 nucleotides is located and the last gene is followed by the trailer region (tr) having a length of 57 nucleotides. The numbers below each gene correspond to the gene length in bp. For the transcription of an individual gene the viral polymerase starts with the synthesis of the mRNA at a conserved sequence at the 3' end referred to as gene-start-motive (GS), followed by a untranslated region (UTR), the open reading frame (ORF) of the viral gene, and finally the gene-end-motive (GE) where the mRNA synthesis stops. Between two expression units a conserved intergenic motiv (I) of 3 by can be found which is not incorporated into the mRNA.

Figure 2:
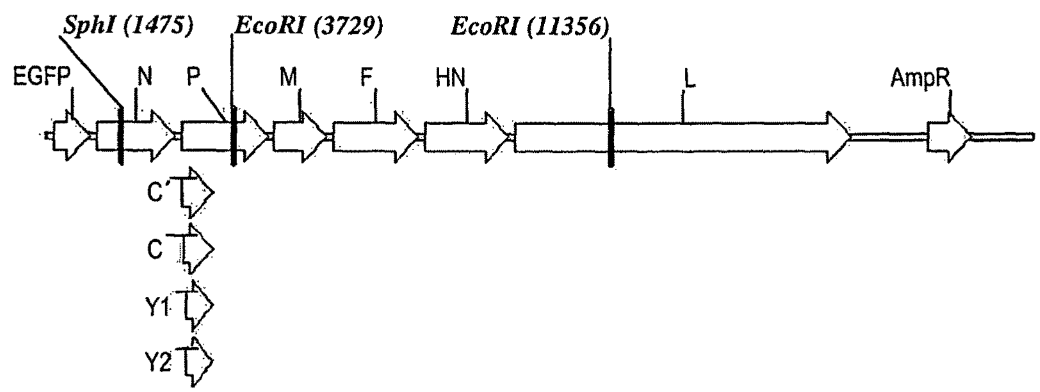
FIG. 2 shows the structure of the pSVV10 plasmide with the cDNA of the Sendai virus.

The basis of the invention is provided in form of the so-called pSVV10 plasmid, more precisely the pSVV10IdGFPMFHN plasmid with a size of 19.774 bp which encodes the cDNA of the Sendai virus of the strain Fushimi, ATCC VR-105. The plasmid is depicted in FIG. 2.

2. Detailed Illustration of the Accessory Proteins Encoded by the P Gene.

Figure 3:
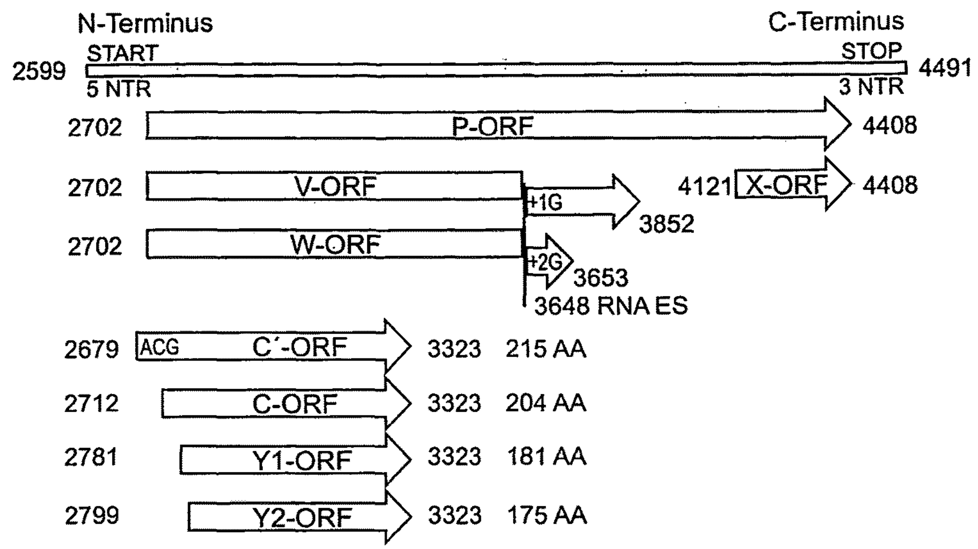
FIG. 3 shows the open reading frames (ORFs) of the non-structural accessory genes in the P gene.

The accessory proteins C', C, Y1, Y2, V and W of the Sendai virus are encoded by the P gene. The ORFs of the C and the Y proteins are shifted by +1 base. The V and W proteins are generated according to the number of the inserted G proteins at the so-called editing site (ES). The P-ORF sequence region with the accessory genes is shown in FIG. 3 where the numbers refer to the specifications in the PSVV10 vector.

3. Subcloning in the Mutagenesis Plasmid

Figure 4:
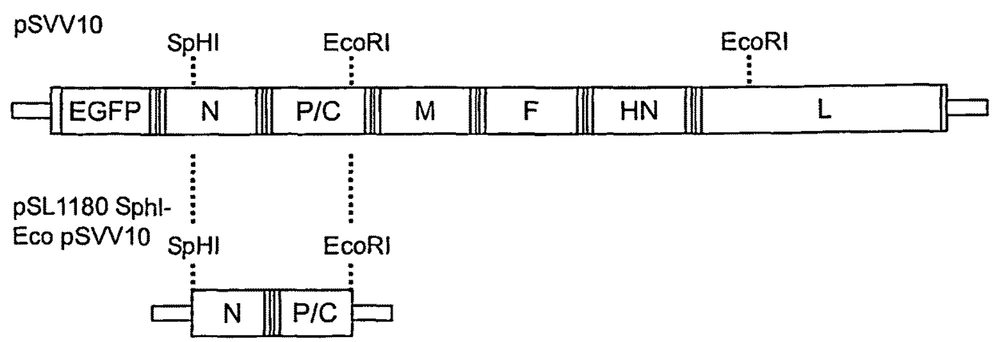
FIG. 4 shows the subcloning into the cloning vector pSL1180.

To insert point mutations into the genes of the accessory proteins a mutagenesis PCR was performed. However, for this method only plasmids having a maximum size of 8 kb can be used. The P/V/C region of the genome of the Sendai virus was subcloned from the Sendai virus vector pSVV10 (19774 bp) via the restriction enzymes EcoRI and SphI into the cloning vector pSL1180 (3422 bp). For this, both of the vectors of pSVV10 (FIG. 2) and pSL1180 were digested with the enzymes EcoRI and SphI and the region of pSVV10 (2254 bp) to be mutated was ligated to the vector backbone of sPL1180 (3303 bp). The resulting cloning plasmid pSL1180 SphI-Eco pSVV10 has a size of 5557 bp; cf. FIG. 4.

4. Mutagenesis

By means of targeted mutation the transcription of the accessory genes C', C, Y1 and Y2 should be prevented. A mutation in the editing site has also the effect that the editing can no longer happen. The following overview shows the relevant cloning area of pSL1180 with all gene starts and the editing site (SEQ ID NO: 19):

```
ACGGCTTCGGCTACACTTACCGCATGGATCAAGATGCCTTCATTCTTAAAGAAGATTCTGAAG

TTGAGAGGGAGGCGCCAGGAGGAAGAGAGTCGCTCTCGGATGTTATCGGATTCCTCGATGCT

GTCCTGTCGAGTGAACCAACTGACATCGGAGGGGACAGAAGCTGGCTCCACAACACCATCAACA

CTCCCCAAGGACCAGGCTCTGCCCATAGAGCCAAAAGTGAGGGCGAAGGAGAAGTCTCAACACC

GTCGACCCAAGATAATCGATCAGGTGAGGAGAGTAGAGTCTCTGGGAGAACAAGCAAGCCAGAG

GCAGAAGCACATGCTGGAAACCTTGATAAACAAAATATACACCGGGCCTTTGGGGGAAGAACTGG

TACAAACTCTGTATCTCAGGATCTGGGCGATGGAGGAGACTCCGGAATCCTTGAAAATCCTCCAA

ATGAGAGAGGATATCCGAGATCAGGTATTGAAGATGAAAACAGAGAGATGGCTGCGCACCCTGAT

AAGAGGGGAGAAGACCAAGCTGAAGGACTTCCAGAAGAGGTACGAGGAGGTACATCCCTACCTG

ATGAAGGAGAAGGTGGAGCAAGTAATAATGGAAGAAGCATGGAGCCTGGCAGCTCACATAGTGC

AAGAG[illegible]CTGGGGTCCTGGTGATTCCTAGCCCCGAACTCGAAGAGGCTGTGCTACGGAGGAAC

AAAAGAAGACCTACCAACAGTGGGTCCAAACCTCTTACTCCAGCAACCGTGCCTGGCACCCGGTC

CCCACCGCTGAATCGTTACAACAGCACAGGGTCACCACCAGGAAAACCCCCATCTACACAGGATG

AGCACATCAACTCTGGGGACACCCCCGCCGTCAGGGTCAAAGACCGGAAACCACCAATAGGGAC
```

-continued

```
CCGCTCTGTCTCAGATTGTCCAGCCAACGGCCGCCCAATCCACCCGGGTCTAGAGACCGACTCA

ACAAAAAAGGGCATAGGAGAGAACACATCATCTATGAAAGAGATGGCTACATTGTTGACGAGTC

TTGGTGTAATCCAGTCTGCTCAAGAATTCGAGTCATCCCGAGACGCGAGTTATGTGTTTGCAAGA

CGTGCCCTAAAGTCTGCAAACTATGCAGAGATGACATTCAATGTATGCGGCCTGATCCTTTCTGCC

GAGAAATCTTCCGCTCGTAAGGTAGATGAGAACAAACAACTGCTCAAACAGATCCAAGAGAGCGT

GGAATCATTCCGGGATATTTACAAGAGATTCTCTGAGTATCAGAAAGAACAGAACTCATTGCTGAT

GTCCAACCTATCTACACTTCATATCATCACAGATAGAGGTGGCAAGACTGACAACACAGACTCCCT

TACAAGGTCCCCCTCCGTTTTTGCAAAATCAAAAGAGAACAAGACTAAGGCTACCAGGTTTGACCC

ATCTATGGAGACCCTAGAAGATATGAAGTACAAACCGGACCTAATCCGAGAGGATGAATTTAGAG

ATGAGATCCGCAACCCGGTGTACCAAGAGAGGGACACAGAACCCAGGGCCTCAAACGCATCACG

CCTCCTCCCCTCCAAAGAGAAGCCCACAATGCACTCTCTCAGGCTCGTCATAGAGAGCAGTCCCC

TAAGCAGAGCTGAGAAAGCAGCATATGTGAAATCATTATCCAAGTGCAAGACAGACCAAGAGGTT

AAGGCAGTCATGGAACTCGTAGAAGAGGACATAGAGTCACTGACCAACTAG
```

ACG = Start C' reading frame of P/W/V + 1
ATG = Start P/W/V reading frame 1
ATG = Start C reading frame of P/W/V + 1
ATG = START Y1 (STOP AT 647) reading frame of P/W/V + 1
ATG = START Y2 reading frame of P/W/V + 1
AAAAAA = EDITING SITE Three specific primers were developed which, on one side, functionally destruct the start sequences of the genes for the accessory proteins, on the other side which do not result in a change of an amino acid in the P reading frame.

```
Primer 1 (SeV C_KO):
5' CGCATGGATCAAGACGCCTTCATTCTAAAAGAAGATTCTGAAGTAGAAGG 3'              (SEQ ID NO: 20)
Unmodified P-amino acids:
                               Asp            Leu                           Val
Orig. P-seq.:  CGC ATG GAT CAA GAT GCC TTC ATT CTT AAA GAA GAT TCT GAA GTT GAG AGG   (SEQ ID NO: 21)
Prim. seq.:    CGC ATG GAT CAA GAC GCC TTC ATT CTA AAA GAA GAT TCT GAA GTA GAG AGG   (SEQ ID NO: 22)
                               Asp            Leu                         Val
Mutated C-amino acids:
                                Start            Leu                       Leu
Modified C-sequence:             ACG CCT TCA TTC TAA AAG AAG ATT CTG AAG TAG AGA GG   (SEQ ID NO: 23)
                                  START             STOP                      STOP

Primer 2 (SeV Y_KO):
5' CTCTCGGACGTTATCGGATTCCTCGACGCTGTCCTG 3'                                (SEQ ID NO: 24)
Unmodified P-amino acids:
                                   Asp                  Asp
P-sequence                     CTC TCG GAC GTT ATC GGA TTC CTC GAC G CT GTC CTG       (SEQ ID NO: 25)
                                   Asp                 Asp
Mutated Y-amino acids:
                                     START                    START
Original sequence                C TCT CGG ATG TTA TCG GAT TCC TCG ATG CTG TCC TG     (SEQ ID NO: 26)
Primer Y1 (C)-sequence           C TCT CGG ACG TTA TCG GAT TCC TCG ACG CTG TCC TG     (SEQ ID NO: 27)
                                     START                    START
```

-continued

```
Primer 3 (SeV Vko):
5' GACTCAACAAAGAAAGGCATAGGTGAGAACACATCATCTATG 3'                    (SEQ ID NO: 28)
Unmodified P-amino acids:
                         Lys      Lys          Gly
Orig. P-seq.:   GAC TCA ACA AAA AAG GGC ATA GGA GAG AAC ACA TCA TCT ATG   (SEQ ID NO: 29)
Prim. seq.:     GAC TCA ACA AAG AAA GGC ATA GGT GAG AAC ACA TCA TCT ATG   (SEQ ID NO: 30)
                            Lys Lys          Gly
Mutated Y-amino acids of V and W:
                                        Lys  Lys    G  H  R   R  E    (SEQ ID NO: 36)
Modified V-sequence:   GAC TCA ACA AAG AAA GGG CAT AGG TGA GAA CAC ATC ATC TAT G  (SEQ ID NO: 31)
(+1G)                                   Lys Lys    G  H  R  STOP      (SEQ ID NO: 37)
                                            Lys Lys    G   A   STOP   (SEQ ID NO: 38)
Modified W-sequence:   GAC TCA ACA AAG AAA GGG GCA TAG GTG AGA ACA CAT CAT CTA TG (SEQ ID NO: 32)
(+2G)
```

With the primers in the mutagenesis PCR the following mutations have been generated: Desired mutations:

| C and C knock-out | Y1 and Y2 knock-out: | Editing site knock-out: | |
|---|---|---|---|
| 4308 T→C | 4377 T→C | 5241 A → G | Editing Site$_{ko}$ |
| C-START$_{ko}$ | Y1-START$_{ko}$ | | |
| 4320 T→A | 4395 T→C | 5244 G → A | |
| C-STOP | Y2-START$_{ko}$ | | |
| 4338 T→A | | 5253 A → T | |
| C-STOP | | | |

The "QuickChange Multi Site directed Kit" of the company Stratagene® enables a targeted insert of point mutations for plasmids of a size of up to 8 kb in three succeeding steps. In the first step the mismatched primers comprising individual point mutations aneal to the denaturated template single strand when given to the reaction. It has to be taken care that all primers bind to the same template strand. The PfuTurbo polymerase, beginning at the primers, extends the complementary sequence without displacing the primers. The newly generated DNA strand now incorporates the mutation and single overhanging ends, so-called "nicks", which are adequately displaced by components of the enzyme Blends.

In the second step a digestion with DpnI is made resulting in a digestion of specifically methylized and hemimethylized DNA. Since plasmids which have been amplified in *Escherichia coli* are dam methylized only the parental template is digested however not the copies generated in the PCR, which contain the mutations.

Figure 5:
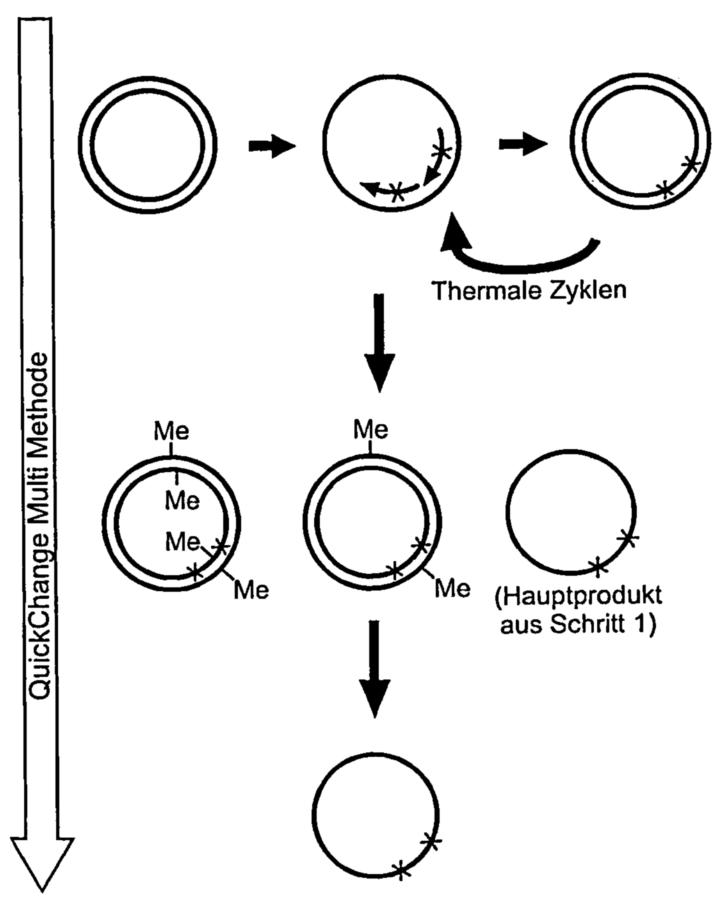
FIG. 5 shows the principle of the mutagenesis PCR.

In the last step the ssDNA is transformed in XL10 gold ultra-competent cells and there converted into dsDNA in vivo. Now the plasmids can be isolated from the bacteria and analyzed for the inserted mutation by means of sequencing. The principle of the mutagenesis PCR is depicted in FIG. 5.

The mutagenesis assay is made up as follows (Tab. 1):

TABLE 1

Assay of the SeV mutagenesis PCR for the generation of recombinant Sendai viruses with partial deletions in the accessory proteins

| Components | Vko | Cko/Yko | Cko/Yko/Vko |
|---|---|---|---|
| 10 x Quick Change Puffer | 2.5 µl | 2.5 µl | 2.5 µl |
| Quick Solution | 0.75 µl | 0.75 µl | 0.75 µl |

TABLE 1-continued

Assay of the SeV mutagenesis PCR for the generation of recombinant Sendai viruses with partial deletions in the accessory proteins

| Components | Vko | Cko/Yko | Cko/Yko/Vko |
|---|---|---|---|
| dNTP Mix | 1 µl | 1 µl | 1 µl |
| QuickChange Mutli Enzyme Blend | 1 µl | 1 µl | 1 µl |
| Plasmid | 100 ng | 100 ng | 100 ng |
| Primer SeV V$_{ko}$ | 0.9 µl | — | 0.9 µl |
| Primer SeV C$_{ko}$ | — | 0.9 µl | 0.9 µl |
| Primer SeV Y$_{ko}$ | — | 0.9 µl | 0.9 µl |
| $H_2O$ | ad 25 µl | ad 25 µl | ad 25 µl |

The mutagenesis PCR resembles a conventional PCR, only the extension time is very long since the complete vector has to be complemented and, therefore, it varies for each vector: Two minutes per kb; here: pSL1180+Eco-SphI fragment from pSVV10~5.5 kb corresponds to 11 minutes extension; cf. Tab. 2:

TABLE 2

Mutagenesis PCR Program

| Mutagenesis PCR | | | |
|---|---|---|---|
| Polymerase activation | 95° C. | 01:00 min | |
| Denaturation | 95° C. | 01:00 min | 35 cycles |
| Annealing | 55° C. | 01:00 min | |
| Extension (depending on Template) | 65° C. | 11:00 min | |
| Extension | 72° C. | 10:00 min | |
| | 4° C. | ∞ | |

Directly after the amplification 1 µl of DpnI restriction enzyme (10 U/µl) is given to the PCR assay, resuspended with the pipette, shortly centrifuged and digested for one hour at 37° C. The resulting ssDNA was transformed into XL10 gold ultra-competent cells and isolated from the bacterial as dsDNA-mutated plasmid by means of Miniprep; cf. Tab.3:

TABLE 3

| Sequence modified by mutagenesis; | | | | |
|---|---|---|---|---|
| | C START | C START | C-STOP | C-STOP |
| WT | //ACG-// | -/-ATG-/- | -/-TTA-/- | -/-TTG-// |
| C' and C (-) | | -C- | -A- | -A- |
| Kurotani* | | | -A- | -A- |
| Gotoh$ | G-- | | -A- | -A- |
| | Y1 START | | Y2 START | |
| WT | //ATGTTA-//-------------- | | /-ATG-// | |
| Y1 and Y2 (-) | - C - | | -C- | |
| Kurotani* | - C - - A - | | -C- | |
| Gotoh$ | - C - - A - | | -C- | |
| | Editing site ko | | STOP STOP | |
| WT | //ACAAAAAAG | | GGC ATA GGA GAG (SEQ ID NO: 39) | |
| Editing site | --G - - A | | - - T | |
| +1G | | | -TGA- | |
| +2G | | | -TGA- | |
| Kurotani* | | | | |
| Gotoh$ | --G - - A | | | |

*Kurutani et al. Genes to Cells, 1998
$Gotoh et al. FEBS letters, 1999

5. Sequencing

Figure 6:
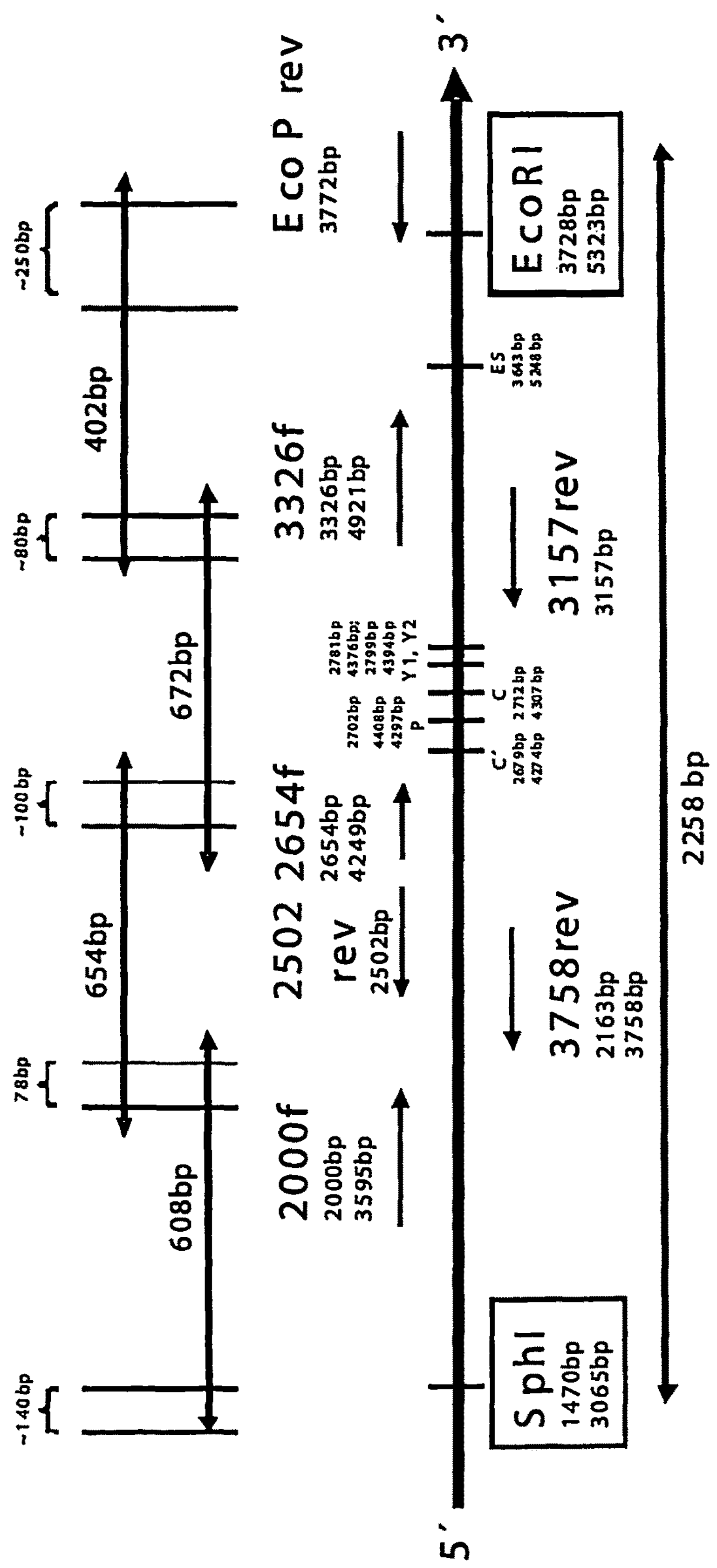
FIG. 6 shows the primer procedure for the verification of the mutations after the mutagenesis PCR.

The resulting mutated plasmids were verified for the correct insert of the mutations. The primer procedure with the inclusion of the entire mutation region is shown in FIG. 6. The upper numbers refer to information for positions in the original vector psVV10 (~19 kb), the lower numbers refer to information for positions in the pSL1180+pSVV10 cloning vector (~5.5 kb).

6. Recloning of the Mutated Sequences into a Vector Encoding for the Complete Sendai Virus The mutated sequence region had to be recloned back into a vector with the complete cDNA sequence of the Sendai virus. Since viruses are to be produced which should have a ubiquitous F cleavage site instead of a cleavage site only activatable by the tryptase "Clara" in the respiratory tract of rodents the eco-eco region of the vector pRS Id-EGFP Fmut (19958 bp, Sascha Bossow, MPI Munich) has been used. Instead of the cleavage site in the F protein of the Sendai virus with the nucleotide sequence (GTTCCACAGTCGAGA; SEQ ID NO: 33) it incorporates a ubiquitous cleavage site of the F protein from the Newcastle disease virus with the sequence (CGTCGTCAGAAGAGA; SEQ ID NO: 34).

Figure 7:
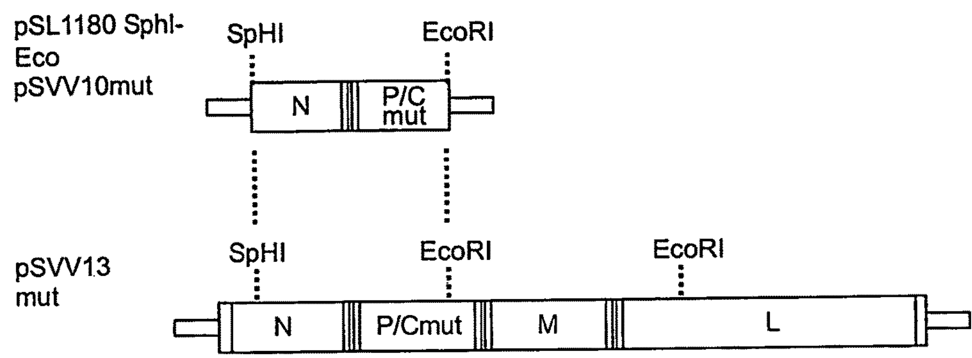
FIG. 7 shows step 1 of the recloning where the mutated SphI-EcoRI fragments were excised from the pLS1180 Sph1-Eco pSVV10 cloning vector and cloned into a Sendai virus vector pVV13.
Figure 8:
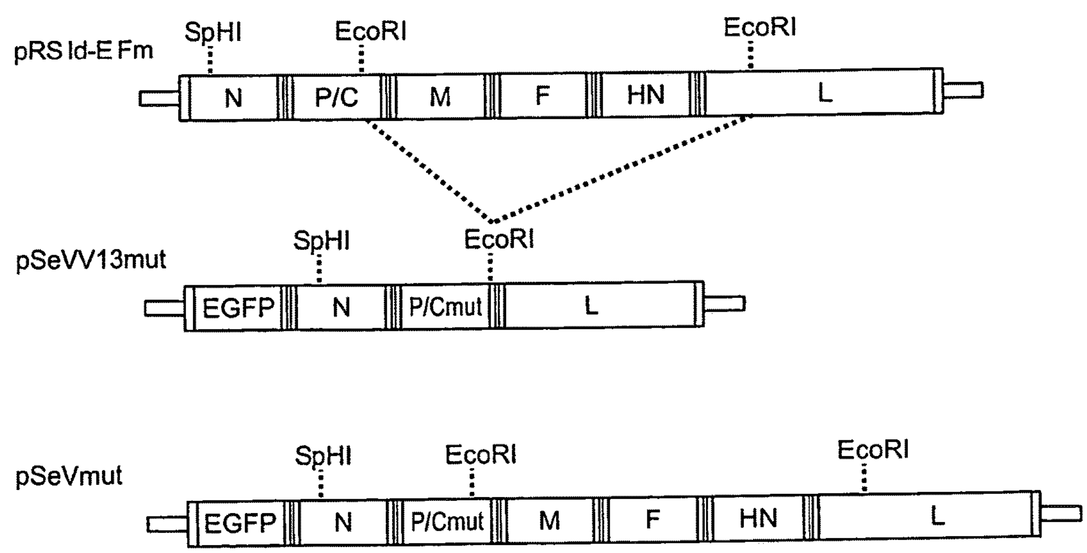
FIG. 8 shows step 2 of the recloning; into the pSVV13 vector lacking of the ORFs for M, F, HN; this region has been cloned with the amended F cleavage site from pRS Id-E Fm via EcoRI; the resulting vectors contain the mutated P/C region and a ubiquitous F cleavage site from NDV.

At first the different mutated SphI-EcoRI fragments were excised from the pSL1180 Sph1-Eco pSVV10 cloning vector and cloned into a Sendai virus vector pSVV13 which is similar to the vector pSVV10, however lack of the regions for the F gene and the HN gene. Then into such vector the lacking regions for the F gene and the HN gene were cloned with the modified cleavage site in the F gene from pRS Id-EGFP Fut via EcoR I. The resulting vectors are referred to as pSeVmut. Functional Sendai viruses were produced by the "rescue" method via the transfection of BSR-T7 cells. Step 1 of the recloning is shown in FIG. 7, and step 2 of the recloning is shown in FIG. 8.

7. Production of Recombinant Sendai Viruses

By the "rescue" method for Paramyxoviridae it is possible to produce genetically modified viruses. For this BSR-T7 cells which constitutively express the T7 RNA polymerase were co-transfected by lipofection with helper plasmids and plasmids encoding the cDNA of the Sendai virus. The plasmids controlled by a T7 promoter are transcribed in the cell resulting, in several steps, in viral proteins and viral negative strand RNA genomes and in the generation of functional viruses.

BSR-T7 cells ($3\times10^5$ per cavity of a plate with six cavities) are seeded and cultivated overnight at 37° C. For the transfection 200 µl of DMEM with FuGENE 6 are put into a vial (the amount of Fugene 6 corresponded to a ratio of 2 µl per µg of DNA) and were incubated for five minutes. After the addition of the DNA components which are listed in the Tab. 4 another incubation step is performed for 25 minutes at room temperature.

TABLE 4

| DNA components of a "rescue" assay | |
|---|---|
| Component | Amount of DNA |
| SeV cDNA | 7.5 µg |
| pTM-N | 250 ng |
| pTM-P/C$^-$ | 150 ng |
| pTM-L | 50 ng |

The BSR-T7 cells were washed for two times with DMEM; in the following 1.8 ml of DMEM medium+2% FCS is provided. The incubated transfection mixture was added dropwise under agitation and the cells were incubated for three days at 33° C. Thereafter the transfected BSR-T7 cells were washed for three times each with 1 ml DMEM to remove plasmid remainders. 1 ml of fresh DMEM medium+2% FCS was added to each assay and the newly generated viruses were harvested after one day.

Before the transfer to Vero cells for the amplification the virus containing supernatant was centrifuged at 300 rpm for four minutes at room temperature. Vero cells which were prepared four days before (plated: $2\times10^5$ cells per 3.5 cm dish; set: approx. $10^6$ cells per 3.5 cm dish at the day of the infection) were two times washed with DMEM and infected with 100 to 500 μl of BSR-T7 supernatant (ad 500 μl adsorption volume with culture medium) for one hour at 33° C. under agitation (every 15 minutes). The inoculum was removed, the cells were washed for two times with DMEM and incubated in 1 ml culture medium for two to five days under daily exchange of medium at 33° C. As soon as eGPF was detectable as viral encoded marker protein in the fluorescence microscope the culture supernatant was removed. With this initial virus passage further passages (passages two and three) were produced at a larger scale. The titer of the virus offspring was quantified by the $TCID_{50}$ method.

The following genetically modified or recombinant Sendai viruses according to the invention were produced:

a) SeV Fmut: Sendai virus Strain Fushimi with NDV cleavage site
b) SeV Fmut dV: as a, in addition with mutations in the V and W genes
c) SeV Fmut dC: as a, in addition with mutations in the C and C' genes
d) SeV Fmut dCdY: as a, in addition with mutations in the C and C' genes and the Y1 and Y2 genes
e) SeV Fmut dCdV: as a, in addition with mutations in the C and C' genes, V and W genes
f) SeV Fmut dCdYdV: as a, in addition with mutations in the C and C' genes, V, W and Y1 and Y2 genes 8. Characterization of the Recombinant Sendai Viruses The generated recombinant Sendai viruses were extensively characterized on several levels. The virus replication was analyzed on non-transformed Vero producer cells and on tumor cells, in particular on hepatoma cells (Hep3B, HuH7, PLC/PRF/5), and on several non-tumor cells such as the human fibroblast cell line MRC 5 and primary human hepatocytes (PHH) of various donors.

Growth Curves

Figure 9:
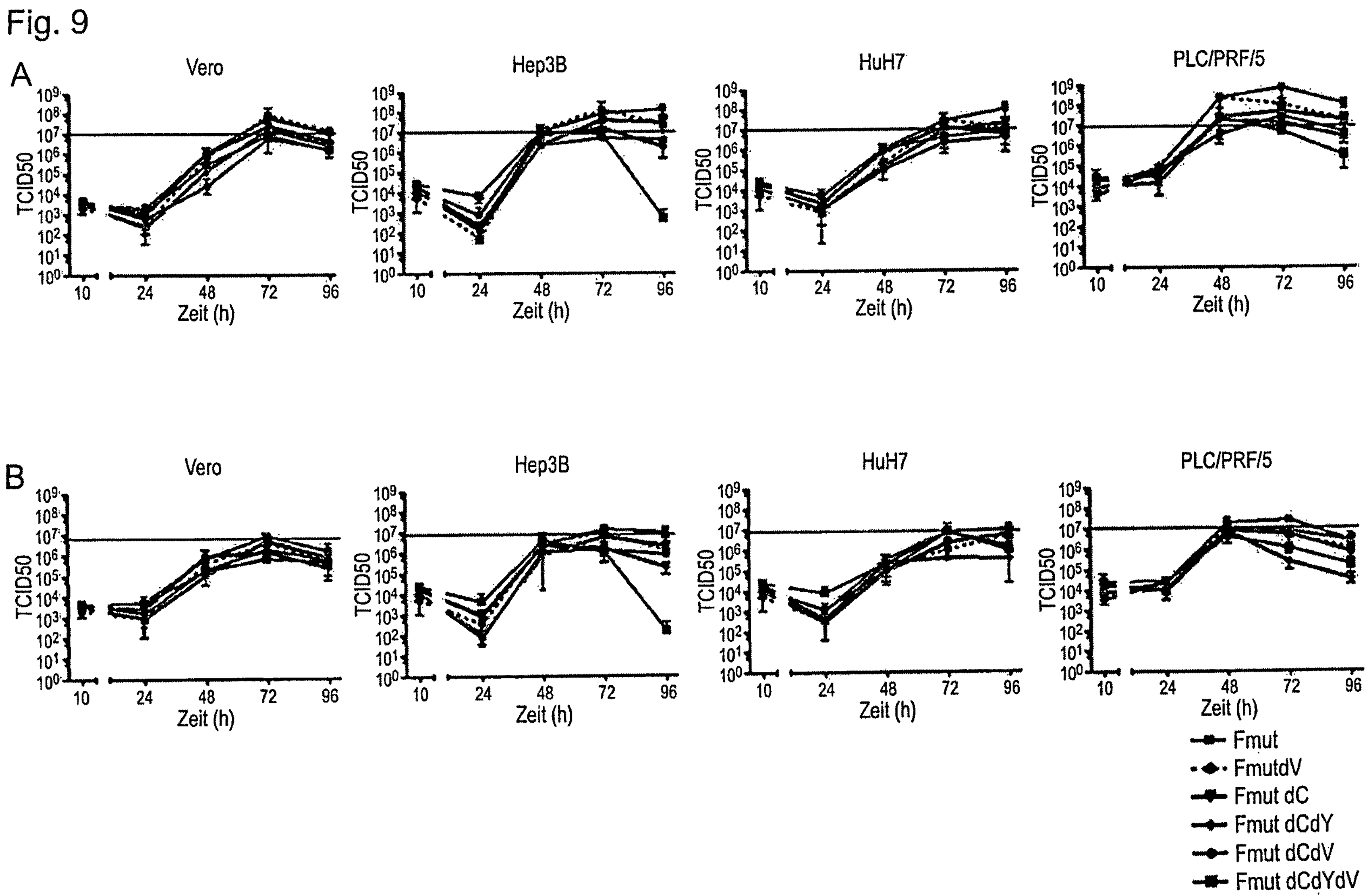
FIG. 9 shows the replication of viruses according to an embodiment of the invention on vero producer cells and hepatoma cells (Hep3B, HuH7, PLC/PRF/5).

1. Provide $1\times10^5$ cells per 12 well in 500 μl (Vero, hepatoma cell, MRC 5, PHH are supplied, also starting from $1\times10^5$ cells)
2. ON growth
3. Remove medium, 1× wash with PBS
4. +250 μl Optimem
5. Dilution of virus in Optimem (MOI 0.05)
6. Add diluted virus to the cells
7. Infect with all 6 SeV variants (freeze excess of the dilutions and titrate as starting value)
8. Infect for 1 h at 37° C.
9. Wash cells 2× (PBS)
10. +1 ml fresh medium (DMEM 5% FCS)
11. Remove viruses in SN after 24, 48, 72 h, 96 h (in each case after infection start) and store at −80° C. (200 μl each)
   a. 2× careful wash with medium
   b. +1000 ml medium (DMEM 5% FCS), scrap off cells
12. Freeze lysates at −80° C.
13. Thaw for titration
   a. 2 min water bath 37° C.
   b. 10-15 sec vortex
   c. 2 min 3000×g small centrifuge
14. Centrifuge
15. Titration on Veros ($TCID_{50}$)
   d. Prepare virus dilutions (first row always diluted)
   e. Add to 96 well plates (always adjust fresh plate to 4° C.)
   f. Trypsinate cells
   g. Count and add $2\times10^4$ cells/96 well
   h. Evaluate titer after 3 days FIG. 9 shows the virus replication on Vero producer cells and hepatoma cells. It is found that all generated recombinant viruses show a very good replication in the Vero producer cells with comparable titers and a virus yield between $10^7$ and $10^8$ $TCID_{50}$/ml.

The titration of the virus particles was repeated in three independent assays, the mean value and the standard deviation are indicated (IO=inoculus).

In the three human standard cell lines for the hepatocellular carcinoma HuH7, PLC/PRF/5 and Hep3B it has been able to demonstrate that all recombinant viruses show a very good replication in tumor cells. Therefore, one decisive precondition for a relevant oncolytic activity of the recombinant viruses according to the invention is fulfilled.

Figure 10:
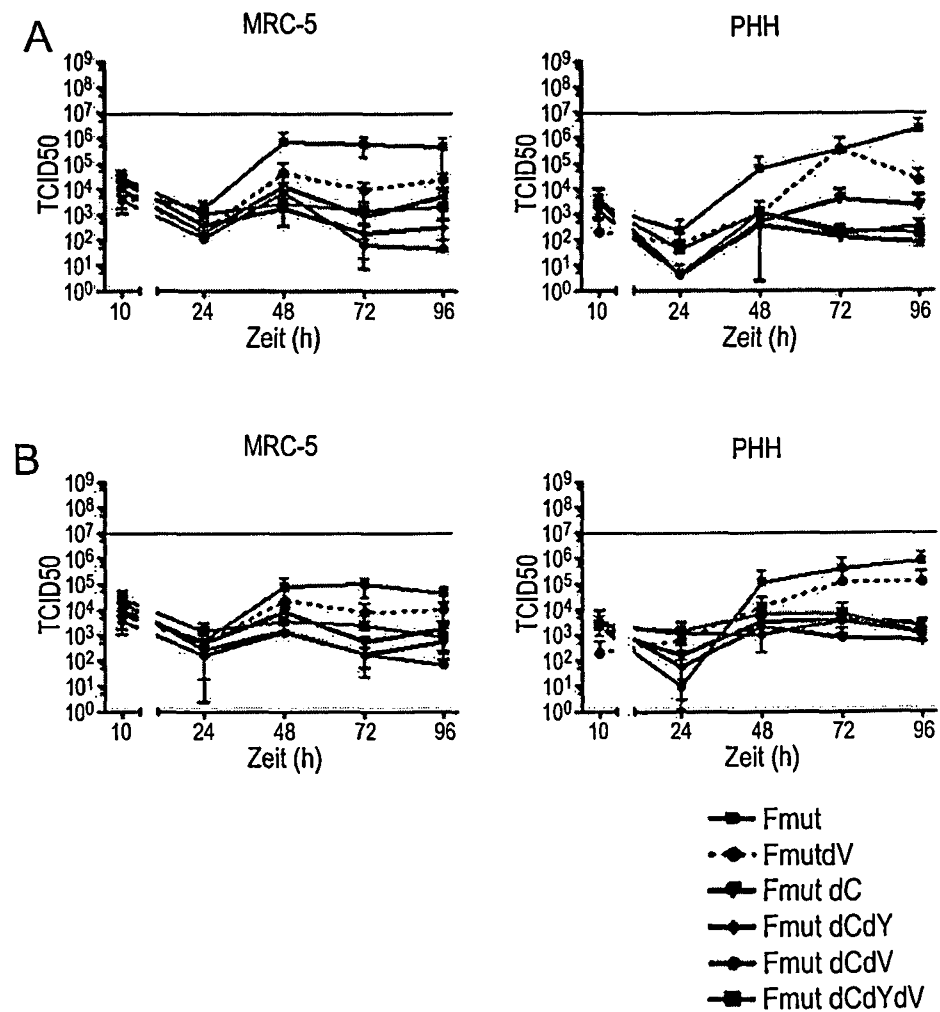
FIG. 10 shows a replication of the viruses according to an embodiment of the invention on non-tumor cells (MRC-5, human fibroblasts; PHH, primary human heptocytes).

The human fibroblast cell line MRC-5 and primary human hepatocytes (PHH) of several different donors were exemplarily analyzed as non-tumor cells. The result is shown in FIG. 10. The intensity of the oncolysis for the analyzed variants occurs in dependence of the deletions in the accessory proteins. Viruses with a single deletion (SeV V F, mut dC, SeV V Fmut dV) have only moderately lost their capability to replicate in normal cells, whereas viruses with two or more deletions (SeV Fmut dCdY, SeV Fmut dCdV, SeV Fmut dCdYdV) replicate effectively in hepatoma cells, i.e. tumor cells, and destruct the latter, however infections in normal cells can hardly be observed.

The titration of the virus particles was repeated in three independent assays (for PHH with three different donors). Indicated are the mean value and the standard deviation (IO—inokulum).

In a further experiment the virus expansion in vivo was analyzed.

1. $5\times10^6$ HuH7 tumor cells were subcutaneously implanted into Balb c nu/nu mice under the right flank
2. Once a tumor volume of at least 100 $mm^3$ has been reached the Sendai virus was administered in 100 μl PBS into the tumor.
3. 2 days after the injection of the virus the animals were sacrificed and the tumors were removed.
4. A part of the tumors was embedded into tissue tack, frozen and cut by a cryotome. GFP expressed by the virus was directly detected in the fluorescence microscope.
5. Another part of the tumors was embedded into paraffin and GFP was detected by specific anti-GFP antibodies.

Figure 11:
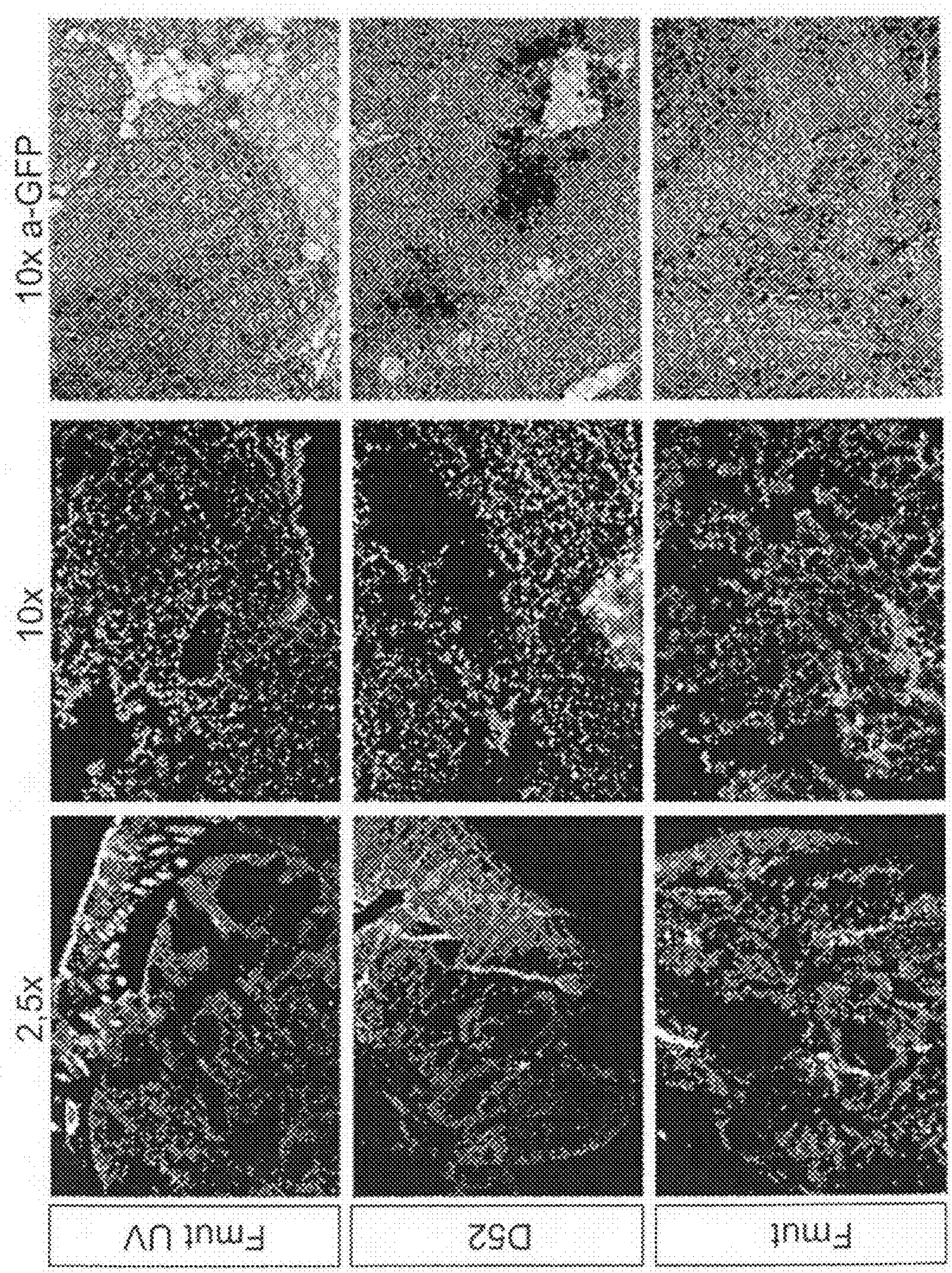
FIG. 11 shows the amplification of the viruses according to an embodiment of the invention in vivo.

The result is shown in FIG. 11. It could have been demonstrated in vivo that the tumor cells are infected by the recombinant virus SeV Fmut and the virus is in a position to expand therein. This result confirms that a replication in vivo outside the lung, as desired, in tumor tissue is possible. SeV Fmut viruses are in a position to proliferate in human hepatoma xenograft tissue (HuH7), D52 viruses ("Fushimi" wild type variants) remain highly locally limited after the virus application into the tumor.

9. Conclusion

The inventors were able to demonstrate by means of different recombinant Sendai viruses which have been genetically modified in respect to the wild type in their F gene and their P gene that they can be used as oncolytic viruses in the anti-tumor therapy.

The following sequences are listed:

SEQ ID NO: 1: Nucleotide sequence of the F gene of SeV (Strain "Ohita")
SEQ ID NO: 2: Amino acid sequence of the F protein of SeV (Strain "Ohita")
SEQ ID NO: 3: Nucleotide sequence of the P gene of SeV (Strain "Ohita")
SEQ ID NO: 4: Amino acid sequence of the P protein of SeV (Strain "Ohita")
SEQ ID NO: 5 Amino acid sequence of the SeV-WT protease cleavage site
SEQ ID NO: 6: Amino acid sequence of the protease cleavage site of the F protein of NDV
SEQ ID NO: 7: Nucleotide sequence of the C' gene of SeV (Strain "Ohita")
SEQ ID NO: 8: Amino acid sequence of the C' protein of SeV (Strain "Ohita")
SEQ ID NO: 9: Nucleotide sequence of the C gene of SeV (Strain "Ohita")
SEQ ID NO: 10: Amino acid sequence of the C protein of SeV (Strain "Ohita")
SEQ ID NO: 11: Nucleotide sequence of the V gene of SeV (Strain "Hamamatsu")
SEQ ID NO: 12: Amino acid sequence of the V protein of SeV (Strain "Hamamatsu")
SEQ ID NO: 13: Nucleotide sequence of the W gene of SeV (Strain "Cantell")
SEQ ID NO: 14: Amino acid sequence of the W protein of SeV (Strain "Cantell")
SEQ ID NO: 15: Nucleotide sequence of the Y1 gene of SeV (Strain "Ohita")
SEQ ID NO: 16: Amino acid sequence of the Y1 protein of SeV (Strain "Ohita")
SEQ ID NO: 17: Nucleotide sequence of the Y2 gene of SeV (Strain "52")
SEQ ID NO: 18: Amino acid sequence of the Y2 protein of SeV (Strain "52")
SEQ ID NO: 19: Nucleotide sequence of the cloning region of pSL1180
SEQ ID NO: 20: Nucleotide sequence PCR primer 1
SEQ ID NO: 21: Nucleotide sequence P gene
SEQ ID NO: 22: Nucleotide sequence P gene mut.
SEQ ID NO: 23: Nucleotide sequence C gene mut.
SEQ ID NO: 24: Nucleotide sequence PCR primer 2
SEQ ID NO: 25: Nucleotide sequence P gene
SEQ ID NO: 26: Nucleotide sequence Y1 gene
SEQ ID NO: 27: Nucleotide sequence Y1 gene mut.
SEQ ID NO: 28: Nucleotide sequence PCR primer 3
SEQ ID NO: 29: Nucleotide sequence P gene
SEQ ID NO: 30: Nucleotide sequence P gene mut.
SEQ ID NO: 31: Nucleotide sequence V gene mut.
SEQ ID NO: 32: Nucleotide sequence W gene mut.
SEQ ID NO: 33: Nucleotide sequence of the cleavage site in the F gene of SeV
SEQ ID NO: 34: Nucleotide sequence of the cleavage site in the F gene of NDV
SEQ ID NO:35: Amino acid sequence of uPa sensitive site
SEQ ID NO:36: Amino acid sequence of mutation to SeV P protein sequence
SEQ ID NO:37: Amino acid sequence of "modified V sequence" mutation
SEQ ID NO:38: Amino acid sequence of "unmodified W sequence" mutation
SEQ ID NO:39: Nucleotide sequenc of the "editing site"in SeV

What is claimed is:

1. A genetically modified oncolytic Paramyxovirus which, in reference to the corresponding wild type (wt), comprises in its F gene at least a first genetic modification and in its P gene at least a second genetic modification, wherein through the second genetic modification the nucleotide sequence encoding at least two accessory non-structural proteins encoded by the P gene is modified, and wherein at least one of the accessory non-structural proteins is selected from the group consisting of C', C, Y1, and Y2.

2. The genetically modified Paramyxovirus of claim 1, wherein the second genetic modification results in a tropism restriction.

3. The genetically modified Paramyxovirus of claim 1, which is a genetically modified Sendai virus (SeV).

4. The genetically modified Paramyxovirus of claim 3, wherein through the first genetic modification a nucleotide sequence encoding a SeV wt protease cleavage site is replaced by a nucleotide sequence encoding a ubiquitous protease cleavage site.

5. The genetically modified Paramyxovirus of claim 4, wherein the ubiquitous protease cleavage site is the cleavage site of the F gene of the Newcastle disease virus (NDV).

6. The genetically modified Paramyxovirus of claim 4, wherein the SeV wt protease cleavage site comprises an amino acid sequence VPQSR (SEQ ID no. 5) and the ubiquitous protease cleavage site comprises an amino acid sequence RRQKR (SEQ ID no. 6).

7. The genetically modified Paramyxovirus of claim 1, wherein through the second genetic modification the nucleotide sequence encoding at least two accessory non-structural proteins is non-transcribable.

8. The genetically modified Paramyxovirus of claim 7, wherein the second genetic modification functionally destroys a start codon of the nucleotide sequence encoding at least two accessory non-structural proteins.

9. The genetically modified Paramyxovirus of claim 1, wherein the second genetic modification functionally destroys at least C or C' and at least Y1 or Y2.

10. The genetically modified Paramyxovirus of claim 1, wherein the second genetic modification functionally destroys at least C or C' and at least V and W.

11. The genetically modified Paramyxovirus of claim 1, wherein the second genetic modification functionally destroys at least C or C' and at least V and W, and at least Y1 or Y2.

12. The genetically modified Paramyxovirus of claim 1, which, in relation to the wt, comprises at least one transgene.

13. The genetically modified Paramyxovirus of claim 12, wherein the transgene is a suicide gene or another gene that induces cell death or an immunostimulating gene.

14. A pharmaceutical composition comprising the genetically modified Paramyxovirus of claim 1 and a pharmaceutically acceptable carrier.

15. A method for the production of a pharmaceutical composition, the method comprising formulating the genetically modified Paramyxovirus of claim 1 into an acceptable carrier.

* * * * *